(12) United States Patent
Schlacter et al.

(10) Patent No.: US 7,553,842 B2
(45) Date of Patent: Jun. 30, 2009

(54) MACROCYCLIC ANALOGS FOR THE TREATMENT OF IMMUNOREGULATORY DISORDERS AND RESPIRATORY DISEASES

(75) Inventors: Stephen T. Schlacter, Boulder, CO (US); John J. Gaudino, Longmont, CO (US); Laurence E. Burgess, Boulder, CO (US); Kevin W. Hunt, Longmont, CO (US)

(73) Assignee: Array Biopharma Inc., Boulder, CO (US)

( * ) Notice: Subject to any disclaimer, the term of this patent is extended or adjusted under 35 U.S.C. 154(b) by 152 days.

(21) Appl. No.: 11/334,858

(22) Filed: Jan. 19, 2006

(65) Prior Publication Data

US 2006/0160838 A1 Jul. 20, 2006

Related U.S. Application Data

(60) Provisional application No. 60/645,552, filed on Jan. 20, 2005.

(51) Int. Cl.
*A01N 43/42* (2006.01)
*A61K 31/44* (2006.01)
*C07D 498/00* (2006.01)
*C07D 221/06* (2006.01)

(52) U.S. Cl. .......................... 514/291; 540/456; 546/79

(58) Field of Classification Search .................... None
See application file for complete search history.

(56) References Cited

U.S. PATENT DOCUMENTS

| | | | | |
|---|---|---|---|---|
| 5,252,732 | A * | 10/1993 | Sinclair et al. .............. | 540/456 |
| 5,284,877 | A * | 2/1994 | Organ et al. ................. | 514/183 |
| 5,457,111 | A * | 10/1995 | Luly et al. .................. | 514/291 |
| 5,563,172 | A | 10/1996 | Wagner et al. | |
| 6,569,867 | B2 | 5/2003 | Chu et al. | |
| 6,624,302 | B2 | 9/2003 | Chu et al. | |
| 2002/0183348 | A1 | 12/2002 | Chu et al. | |

FOREIGN PATENT DOCUMENTS

| | | |
|---|---|---|
| GB | 2 245 891 A | 1/1992 |
| WO | WO 95/09857 | 4/1995 |

OTHER PUBLICATIONS

"PDR Electronic Library™: Stedman Definition", http://www.thomsonhc.com/pdrel/librarian/PFActionId/pdrcommon.stedmans.StedmansDocumentAction/DocumentDefinition/pdrcommon.Stedmans/DocumentId/11633/SBK/3/PFPUI/Xm1qVKg1QTxkjh/CS/B6F30D (accessed May 3, 2007).*
Clemons et al. Chemistry and Biology, 2002, 9, 49-61.*
Wang-Fen et al. Journal of Chromatography A, 2001, 925, 139-49.*
Vippagunta et al. Advanced Drug Delivery Reviews, 2001, 48, 3-26.*
Nelson, et al. "Rhodium-carbenoid-mediated intermolecular O-H insertion reactions: a dramatic additive effect. Application in the synthesis of an ascomycin derivative"; Tetrahedron Letters, Elsevier Science Ltd.; 2000; pp. 1877-1881.
Shafiee et al., "Enzymatic Synthesis and Immunosuppresive Activity of Novel Desmethylated Immunomycins (Ascomycins)"; *J. of Antibiotics*, vol. 46, No. 9, pp. 1397-1405 (1993).

* cited by examiner

*Primary Examiner*—James O Wilson
*Assistant Examiner*—Noble Jarrell
(74) *Attorney, Agent, or Firm*—John R. Moore; Viksnins Harris & Padys

(57) ABSTRACT

Disclosed are compounds of the Formula I

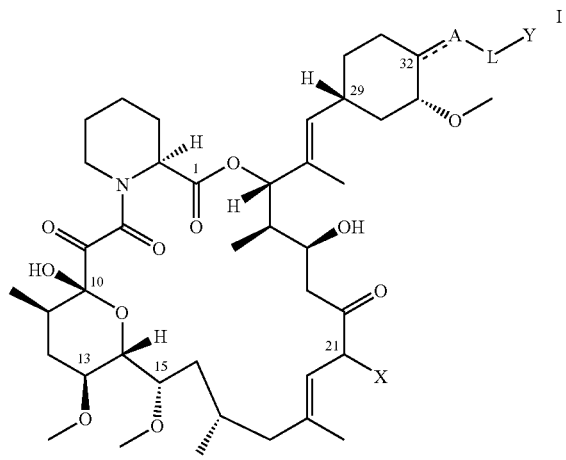

and diastereomers, tautomers, solvates, metabolites, and pharmaceutically acceptable salts thereof, wherein X, A, L and Y are as defined herein. Such compounds are useful in the treatment of immunoregulatory and respiratory diseases in mammals. Also disclosed are methods of using such compounds in the treatment of immunoregulatory and respiratory diseases in mammals and pharmaceutical compositions containing such compounds.

26 Claims, No Drawings

MACROCYCLIC ANALOGS FOR THE TREATMENT OF IMMUNOREGULATORY DISORDERS AND RESPIRATORY DISEASES

CROSS-REFERENCE TO RELATED APPLICATIONS

This application claims priority to U.S. Provisional Application Ser. No. 60/645,552, filed Jan. 20, 2005, which is incorporated herein by reference in its entirety.

BACKGROUND OF THE INVENTION

1. Field of the Invention

This invention relates to novel FK520 and FK506 analogs and other similar calcineurin inhibitors, methods for making these analogs, and their use for treating immunoregulatory and respiratory diseases, disorders, and conditions.

2. Description of the State of the Art

FK520, originally called ascomycin, is a substantial component of a large family of macrocyclic fermentation products. This family, originally isolated from cultures of *Streptomyces hygroscopicus* var. *ascomyceticus* (T. Arai, et al., *J. Antibiotics* (Tokyo) 15 (Ser. A), 231-232 (1962)), is produced as a group of secondary fungal metabolites. Ascomycin was initially pursued for its antifungal activities but it is also an effective immunosuppressant, acting primarily through T-lymphocytes via inhibition of the phosphatase calcineurin. Ascomycin reduces the production of a range of cytokines, inhibiting the activation of various cell types, including those involved in cell-mediated immunity. Due to these properties, ascomycin remains an interesting substrate for development of therapeutics in the transplantation field. This molecule is a close chemical analog of FK506 (tacrolimus), which is currently utilized as a first-line therapy for transplantation rejection.

In addition to its wide use to prevent and treat organ transplant rejection, the FK family of molecules has been evaluated in a large range of disorders linked to immunoregulatory dysfunction and respiratory diseases. FK506, along with other calcineurin inhibitors (for example, cyclosporin A), has been used for the treatment of nephritic syndrome, active Crohn's disease, acute ocular Behcet syndrome, endogenous uveitis, psoriasis, atopic dermatitis, rheumatoid arthritis, aplastic anemia, primary biliary cirrhosis, celiac disease and other immunoregulatory diseases. Limited evidence suggests cyclosporin is effective in patients with intractable pyoderma gangrenosum, polymyostitis/dermatomyositis or severe corticosteroid-dependent asthma (D. Faulds, et al., *Drug Evaluation*, 45:953 (1993) and P. J. Wahab, et. al., *Aliment Pharmacol Ther.*, 14:767 (2000)). Other immunosuppressants (e.g., FK520 analogs, for example Elidel) are effective for these disease states. The effect of FK506 and other calcineurin inhibitors (e.g., FK520 analogs, cyclosporin) on inflammatory cells and their mediators make it a promising therapy for asthma, chronic obstructive pulmonary disease (COPD), idiopathic pulmonary fibrosis (IPF), and other lung diseases. Treatment of these disorders with potent immunosuppressants such as cyclosporin or FK506 is currently limited to patients with severe disease that are either refractory or hypersensitive to standard treatments. This limitation is due to adverse events of treatment, including, but not limited to, hypertrichosis, gingival hyperplasia, neurological effects, gastrointestinal effects, and renal dysfunction. Chronic treatment with calcineurin inhibitors requires frequent renal function monitoring due to increased incidence of kidney failure.

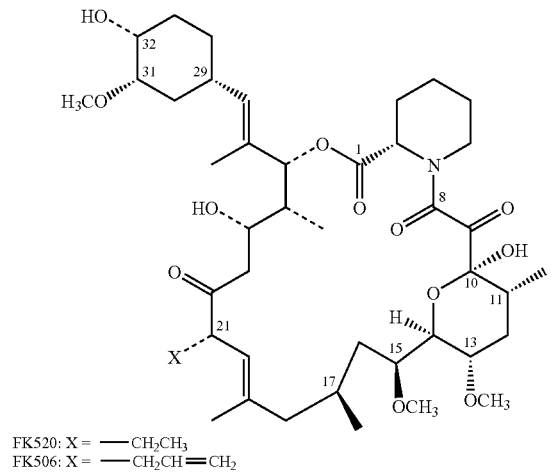

FK520: X = —CH$_2$CH$_3$
FK506: X = —CH$_2$CH=CH$_2$

The mechanism of toxicity of unmodified calcineurin inhibitors such as FK520, FK506 and cyclosporin has been related to the mechanism of immunosuppression (F. J. Dumont, et al., *J. Exp. Med.*, 176:751-760 (1992). This strong link between the mechanism of action and the many macrocyclic-induced toxicities has presented a significant challenge to improving the therapeutic index of FK506, FK520 and cyclosporin through chemical modification. Indeed, efforts to date have failed to separate the efficacy of these molecules from their systemic toxicities. Segregation of efficacy and toxicity of new analogs might still be possible by altering a compound's distribution or metabolism (N. H. Signal, et. al., *J. Exp. Med.*, 173:619 (1991)). By limiting the exposure and potential toxicity of an active calcineurin inhibitor to organs that are sensitive to such inhibition (e.g., kidney), system toxicity can be avoided. At the same time, the topical exposure of the active calcineurin inhibitor at a required site of action in diseased tissues and organs (skin, lung, gut, eye, etc.) can be maximized.

SUMMARY OF THE INVENTION

This invention provides for novel, topically active FK520 and FK506 analogs and other similar calcineurin inhibitors, which are useful in the treatment of immunoregulatory and respiratory diseases, disorders and conditions.

More specifically, one embodiment of the present invention provides compounds of the Formula I:

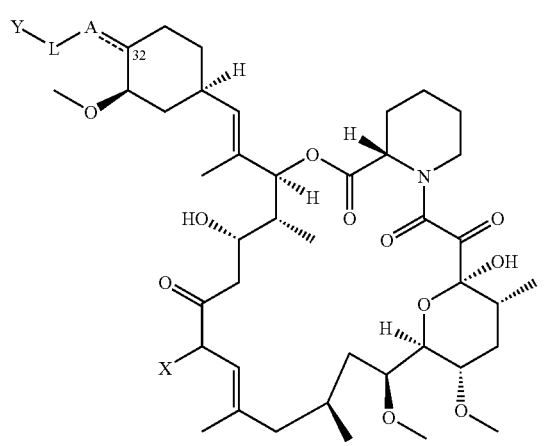

and diastereomers, tautomers, solvates, metabolites and pharmaceutically acceptable salts thereof, wherein:

the dashed line is an optional double bond;

X is alkyl, alkenyl, or alkynyl, wherein said alkyl, alkenyl and alkynyl are optionally substituted with one or more groups independently selected from F, Cl, Br, I, aryl, $COOR^1$, and a fully unsaturated or partially unsaturated five or six-membered heterocyclic ring having one to four heteroatoms independently selected from N, O and S, wherein said heterocyclic ring is optionally substituted with oxo;

A is O, S, $CH_2$ or CH, or A represents a carbon atom and an oxygen atom each bonded to carbon 32 of Formula I and which together complete a saturated or partially unsaturated five, six or seven membered spirocyclic lactone ring;

Y is absent, H, $R^3$—SC(=O) or $R^3$—OC(=O), or Y is

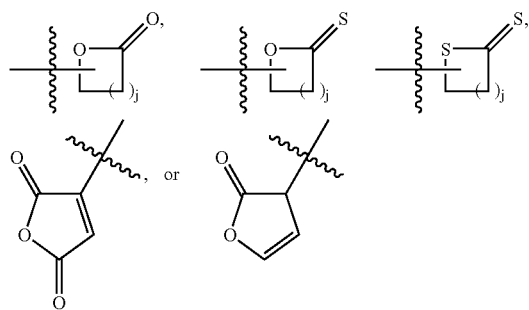

wherein said Y groups are optionally substituted with one or more groups independently selected from alkyl, alkenyl, alkynyl, $OR^4$, $SR^4$, and $NR^4R^5$;

L is absent, alkylene, $Z_m$-E-Z, $NR^2C$(=O)Z, C(=O)$NR^2Z$, B—Ar—(CH=CH)$_m$—(CH$_2$)$_p$,D-Ar—$NR^2C$(=O), OArC(=O)CH$_2$ or S-Z-NHC(=O);

Z is $C_1$-$C_4$ alkylene optionally substituted with one or more groups selected from alkyl, F, Cl, Br and I;

Ar is arylene optionally substituted with one or more groups independently selected from F, Cl, Br and I;

B is O, S, or CH$_2$;

D is CH$_2$, O, S, SO, or SO$_2$;

E is O, S, $NR^2$, or OC(=O);

m is 0 or 1;

j is 1, 2, 3, 4, or 5;

$R^1$ is H, alkyl, alkenyl, alkynyl, or aryl, wherein said aryl is optionally substituted with one or more groups independently selected from F, Cl, Br and I;

$R^2$ is H or alkyl;

$R^3$ is alkyl, alkenyl, or alkynyl, wherein said alkyl, alkenyl, and alkynyl are optionally substituted with one or more groups independently selected from F, Cl, Br, and I; and $R^4$ and $R^5$ are independently H, alkyl or aryl.

The invention also includes diastereomers, tautomers, solvates, metabolites, and pharmaceutically acceptable salts of compounds of Formula I. Methods of making the compounds of Formula I are also described.

The inventive compounds may further be used advantageously in combination with other known therapeutic agents.

The invention also relates to pharmaceutical compositions comprising an effective amount of a compound selected from compounds of Formula I, or a diastereomer, tautomer, solvate, metabolite or pharmaceutically acceptable salt thereof.

Another aspect of the invention provides methods of preventing or treating an immunoregulatory disease, disorder, or condition in a mammal, comprising administering to a mammal in need of such treatment an effective amount of a compound of Formula I or a diastereomer, tautomer, solvate, metabolite, or pharmaceutically acceptable salt thereof. In certain embodiments, administration is via topical, inhalation, ocular, oral or rectal routes.

In a further aspect the present invention provides a method of using a compound of this invention as a medicament to treat or prevent immunoregulatory or respiratory diseases, disorders and conditions in a mammal. In certain embodiments, administration is via topical, inhalation, ocular, oral or rectal routes.

An additional aspect of the invention is the use of a compound of Formula I or a diastereomer, tautomer, solvate, metabolite, or pharmaceutically acceptable salt thereof in the preparation of a medicament for the treatment or prevention of immunoregulatory and respiratory diseases, disorders and conditions in a mammal.

Another aspect of the invention includes kits comprising a compound of Formula I, or a diastereomer, tautomer, solvate, metabolite, or pharmaceutically acceptable salt thereof, a container, and optionally a package insert or label indicating a treatment.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, cyclopropyl, cyclobutyl, cyclopentyl, cyclohexyl, cycloheptyl, and cyclooctyl.

The term "alkylene" as used herein refers to a linear or branched saturated divalent hydrocarbon radical of one to twelve carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), 1-propenyl, 1-butenyl, 2-butenyl, and the like.

The term "alkenylene" as used herein refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH$_2$C≡CH).

The term "alkynylene" as used herein refers to a linear or branched divalent hydrocarbon radical of two to twelve carbons containing at least one triple bond, wherein the alkynylene radical may be optionally substituted independently with one or more substituents described herein. Examples include, but are not limited to, ethynylene, propynylene, and the like.

The terms "carbocycle", "carbocyclyl" and carbocyclic ring refer to a monovalent non-aromatic, saturated or partially unsaturated ring having 3 to 12 carbon atoms as a monocyclic ring or 7 to 12 carbon atoms as a bicyclic ring. Spirocyclic moieties are included in the scope of this definition. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated ring, a partially unsaturated ring, or an aromatic ring. Typical aryl groups include, but are not limited to, radicals derived from benzene, substituted benzenes, naphthalene, anthracene, biphenyl, indenyl, indanyl, 1,2-dihydronapthalene, 1,2,3,4-tetrahydronapthyl, and the like.

The term "arylene" refers to a divalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally substituted with one or more groups selected from, e.g., halogen, alkyl, alkoxy, trifluoromethyl, aryl, heteroaryl, and hydroxy.

The terms "heterocycle," "hetercyclyl" and "heterocyclic ring" are used interchangeably herein and refer to a saturated or a partially unsaturated (i.e., having one or more double and/or triple bonds within the ring) carbocyclic radical of 3 to 8 ring atoms in which at least one ring atom is a heteroatom selected from nitrogen, oxygen and sulfur, the remaining ring atoms being C, where one or more ring atoms is optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a carbocyclic, heterocyclic, aromatic or heteroaromatic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Example of a heterocyclic group wherein 2 ring carbon atoms are substituted with oxo (=O) moieties are pyrimidinonyl and 1,1-dioxo-thiomorpholinyl. The heterocycle groups herein are unsubstituted or substituted in one or more substitutable positions with various groups.

The term "heteroaryl" refers to a monovalent aromatic radical of 5-, 6-, or 7-membered rings and includes fused ring systems (at least one of which is aromatic) of 5-10 atoms containing one or more heteroatoms selected from nitrogen, oxygen, and sulfur. Examples of heteroaryl groups are pyridinyl (including, for example, 2-hydroxypyridinyl), imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spirocyclic moieties are also included within the scope of this definition. Heteroaryl groups are optionally substituted independently with one or more substituents described herein.

By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" represents fluorine, bromine, chlorine, and iodine.

"Substituted alkyl", "substituted alkenyl", "substituted alkynyl", "substituted aryl", "substituted heteroaryl", "substituted heterocyclyl" and "substituted cycloalkyl" mean alkyl, alkenyl, alkynyl, aryl, heteroaryl, heterocyclyl and cycloalkyl, respectively, in which one or more hydrogen atoms are each independently replaced with a substituent. Typical substituents include, but are not limited to, F, Cl, Br, I, CN, $CF_3$, OR, R, =O, =S, =NR, =$N^+$(O)(R), =N(OR), =$N^+$(O)(OR), =N—NRR', —C(=O)R, —C(=O)OR, —C(=O)NRR', —NRR', —$N^+$RR'R", —N(R)C(=O)R', —N(R)C(=O)OR', —N(R)C(=O)NR'R", —SR, —OC(=O)R, —OC(=O)OR, —OC(=O)NRR', —OS($O)_2$(OR), —OP(=O)$(OR)_2$, —OP$(OR)_2$, —P(=O)$(OR)_2$, —P(=O)(OR)NR'R", —S(O)R, —S$(O)_2$R, —S$(O)_2$NR, —S(O)(OR), —S$(O)_2$(OR), —SC(=O)R, —SC(=O)OR, =O and —SC(=O)NRR'; wherein each R, R' and R" is independently selected from H, $C_1$-$C_{10}$ alkyl, $C_1$-$C_{10}$ alkenyl, $C_1$-$C_{10}$ alkynyl, $C_6$-$C_{20}$ aryl and $C_2$-$C_{20}$ heterocycle.

The term "a" means one or more.

The terms "compound(s) of this invention" and "compound(s) of Formula I" include compounds of Formula I and diastereomers, tautomers, solvates, metabolites, and pharmaceutically acceptable salts thereof.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Macrocyclic Compounds of Formula I

The present invention provides compounds of Formula I, which are useful in the treatment of immunoregulatory and respiratory diseases. The present invention applies the "soft drug" concept to the preparation of the compounds of Formula I. This approach limits the exposure of a calcineurin inhibitor of this invention to organs that are sensitive (i.e., kidney) and results in toxicities while maximizing the topical exposure of the active calcineurin inhibitor to diseased tissues and organs (e.g., skin, lung, gut, eye, etc.).

A soft drug, or antedrug, is a compound that is a close structural analog of a known active drug that possesses a specific metabolic liability that provides a predictable, controlled detoxification (N. Bodor, P. Buchwald; Med. Res. Rev. (2000) 20:58). Most soft drugs are designed to act topically at the site of application and to be rendered inactive upon entering systemic circulation (see, for example, T. Lazarova, et al., J. Med. Chem. 46:674 (2003) and T. H. Keller, et al., in New Drugs for Asthma, Allergy and COPD; Hansel, T. T., Barnes, P. J., Eds.; Progress in Respiratory Research, Vol. 31; Karger; Basel, Switzerland 2003; pp 237-240).

Applying soft drug principles to FK520, FK506 and other similar calcineurin inhibitors allows the segregation of its efficacy in immunoregulatory disorders (lung, skin, eye, gut, nasal, colonic, ear, oral, vaginal diseases) from its use-limiting toxicity. A "soft" analog of FK520, FK506 and other similar calcineurin inhibitors, such as a compound of Formula I, is highly desirable, given the current lack of safe and efficacious treatment options for immunoregulatory disorders and severe lung diseases. Accordingly, the compounds of Formula I include "soft" analogs of all naturally occurring FK analogs, for example "soft" analogs of FK520 and FK506, in addition to analogs accessible by total synthesis, fermentation, enzymatic catalysis, and/or genetic engineering.

By provision of the analogs of the invention which are topically active, but systemically inactive, the present invention makes potent immunosuppressant therapy available to subjects for whom such therapy might otherwise be excluded due to the unacceptable risk of systemic side effect(s). The analogs of this invention demonstrate comparable therapeutic profiles and mechanisms of action to marketed immunosuppressants such as FK506, Elidel and cyclosporin, without the accompanying toxicities.

In general, one embodiment of the invention relates to compounds having the general Formula I:

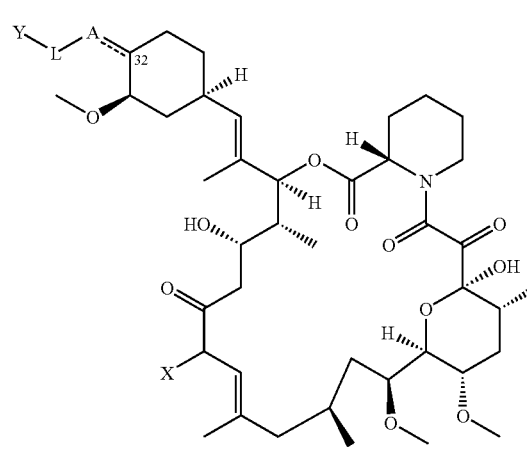

and diastereomers, tautomers, solvates, metabolites, and pharmaceutically acceptable salts thereof, wherein:

the dashed line is an optional double bond;

X is alkyl, alkenyl, or alkynyl, wherein said alkyl, alkenyl and alkynyl are optionally substituted with one or more groups independently selected from F, Cl, Br, I, aryl, COOR¹, and a fully unsaturated or partially unsaturated five or six-membered heterocyclic ring having one to four heteroatoms independently selected from N, O and S, wherein said heterocyclic ring is optionally substituted with oxo;

A is O, S, CH₂ or CH, or A represents a carbon atom and an oxygen atom each bonded to carbon 32 of Formula I and which together complete a saturated or partially unsaturated five, six or seven membered spirocyclic lactone ring;

Y is absent, H, R³—SC(=O) or R³-OC(=O), or Y is

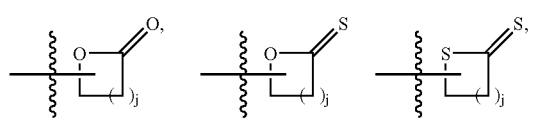

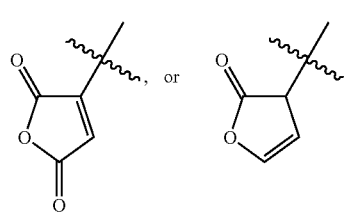

wherein said Y groups are optionally substituted with one or more groups independently selected from alkyl, alkenyl, alkynyl, OR⁴, SR⁴, and NR⁴R⁵;

L is absent, alkylene, $Z_m$-E-Z, NR²C(=O)Z, C(=O) NR²Z, B—Ar—(CH=CH)$_m$—(CH₂)$_p$, D-Ar—NR²C(=O), OArC(=O)CH₂ or S-Z-NHC(=O);

Z is C₁-C₄ alkylene optionally substituted with one or more groups selected from alkyl, F, Cl, Br or I;

Ar is arylene optionally substituted with one or more groups independently selected from F, Cl, Br and I;

B is O, S, or CH₂;

D is CH₂, O, S, SO, or SO₂;

E is O, S, NR², or OC(=O);

m is 0 or 1;

j is 1, 2, 3, 4, or 5;

R¹ is H, alkyl, alkenyl, alkynyl, or aryl, wherein said aryl is optionally substituted with one or more groups independently selected from F, Cl, Br and I;

R² is H or alkyl;

R³ is alkyl, alkenyl, or alkynyl, wherein said alkyl, alkenyl, and alkynyl are optionally substituted with one or more groups independently selected from F, Cl, Br, and I; and R⁴ and R⁵ are independently H, alkyl or aryl.

Exemplary embodiments of compounds of Formula I include the structures

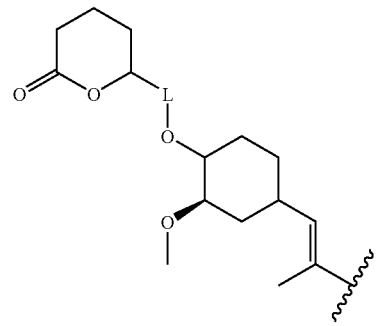

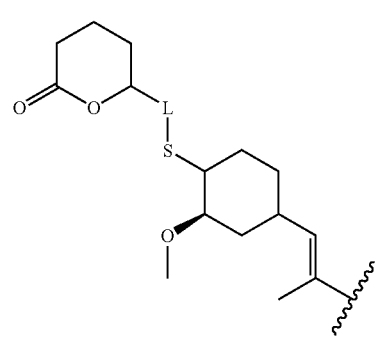

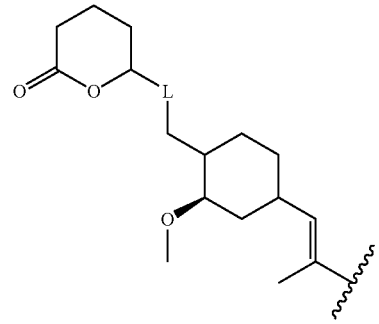

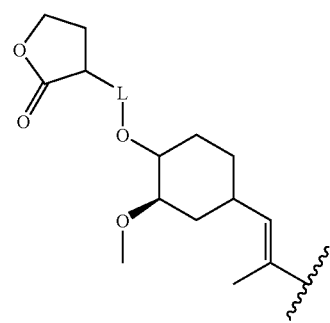

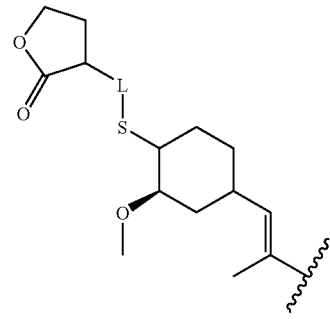

-continued
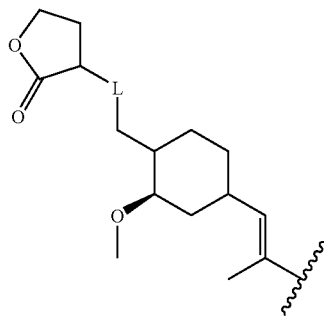
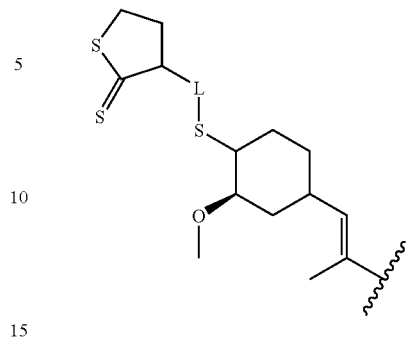
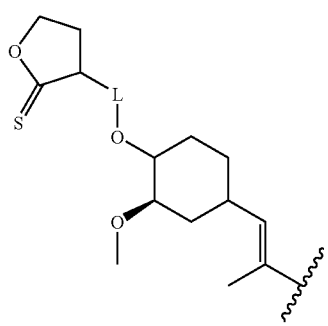
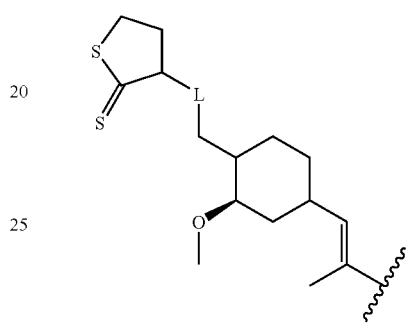
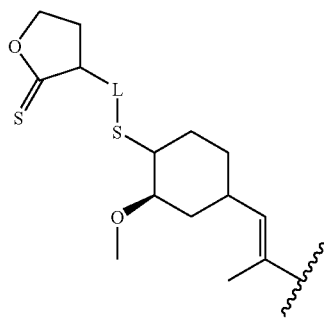
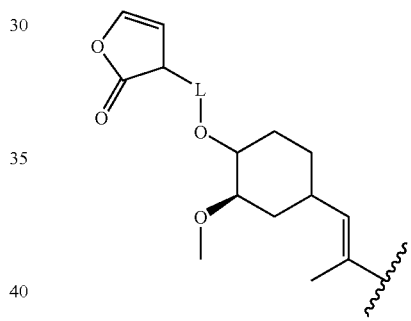
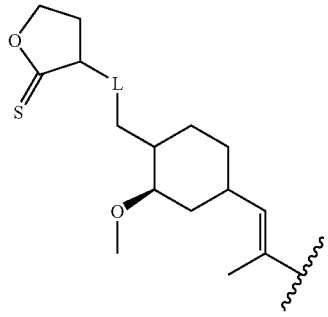
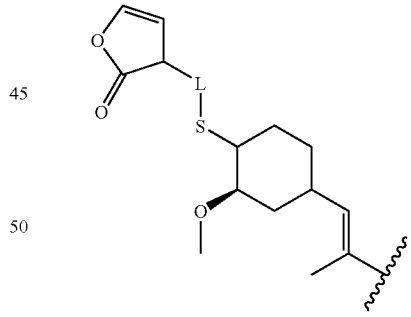
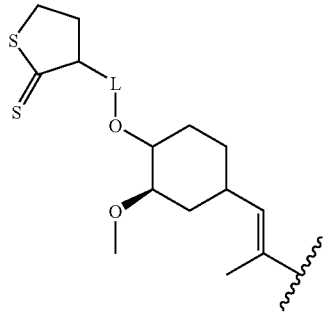
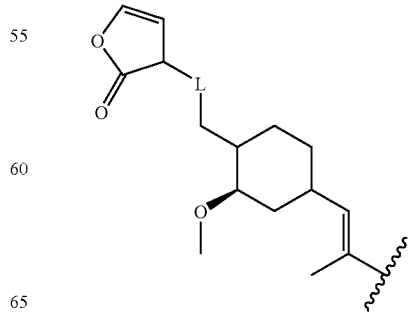

-continued
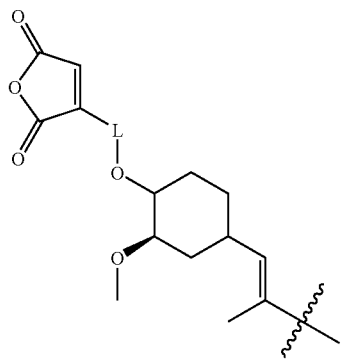
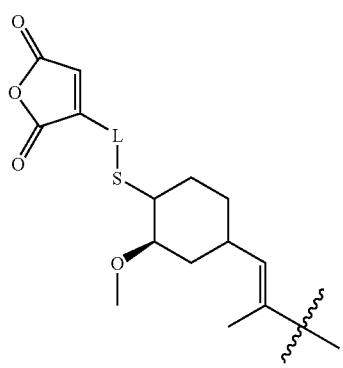
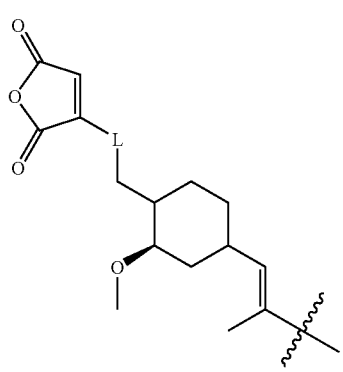
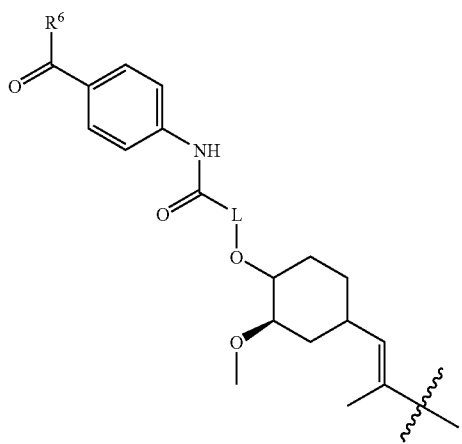
-continued
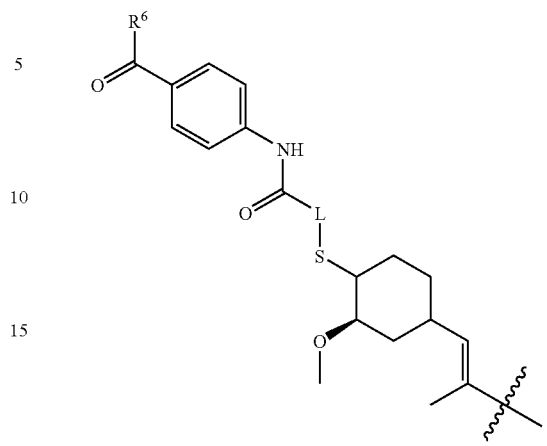
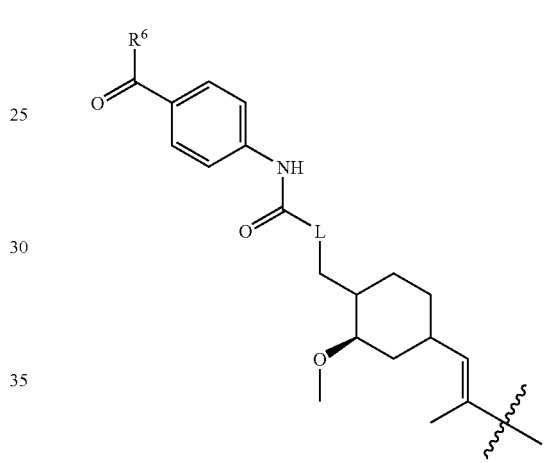
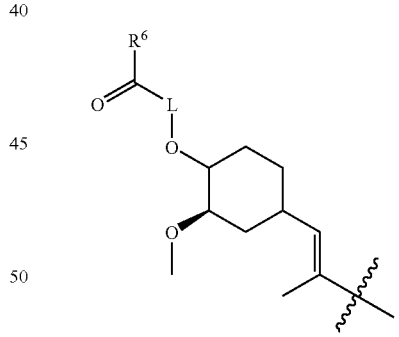
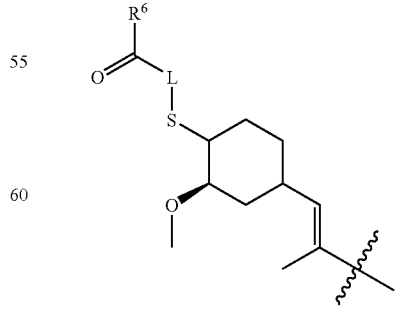

-continued

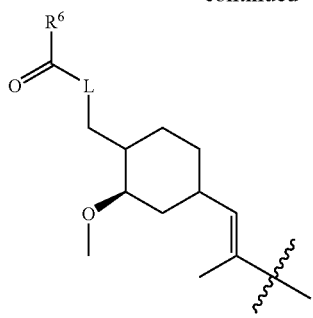

wherein the wavy line indicates the point of attachment to a macrocyclic core, wherein said macrocyclic core has the structure:

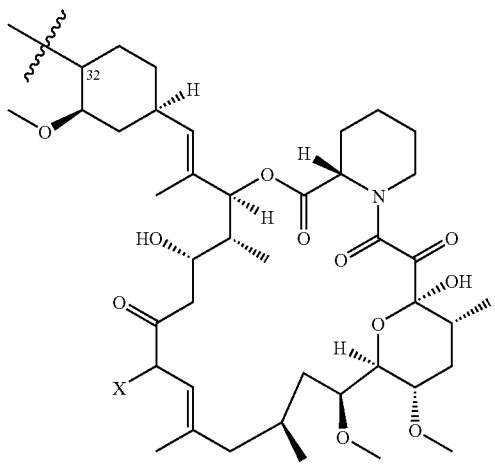

In certain embodiments, L is absents. In other embodiments, L is optionally substituted alkylene. For example, in certain embodiments L is methylene, ethylene, propylene, or butylene, or substituted forms thereof.

In certain embodiments, L is $Z_m$-E-Z. Exemplary embodiments include the structures

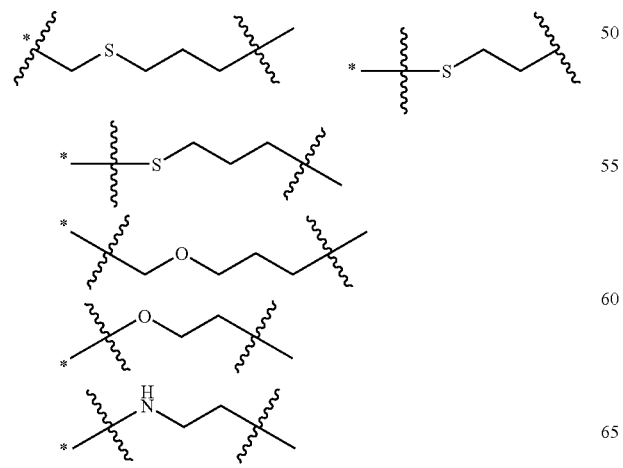

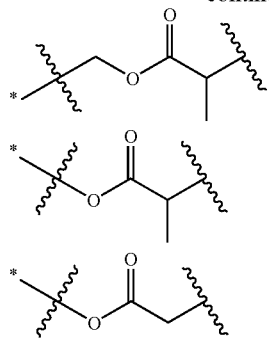

wherein the asterisk indicates the point of attachment to Y.

In certain embodiments, L is $NR^2C(=O)Z$. Exemplary embodiments include the structures

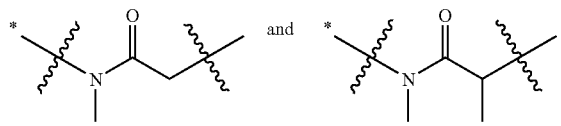

wherein the asterisk indicates the point of attachment to Y.

In certain embodiments, L is B—Ar—(CH=CH)$_m$—(CH$_2$)$_p$. Exemplary embodiments include the structures

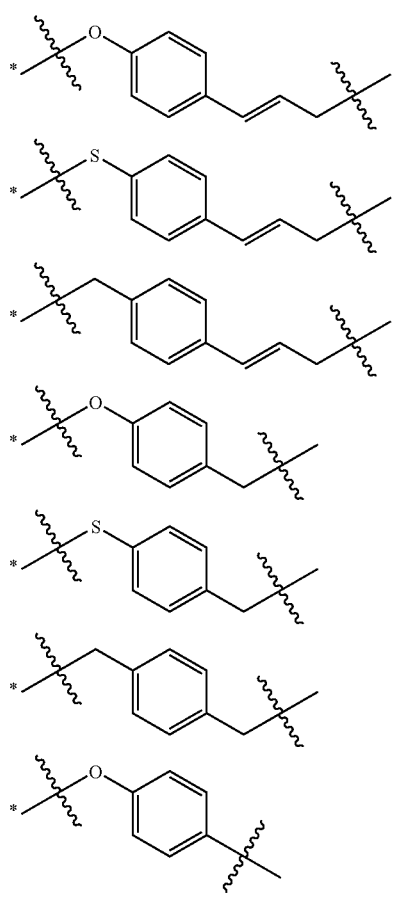

-continued

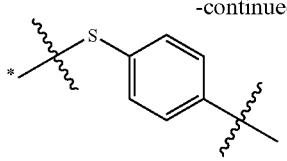

wherein the asterisk indicates the point of attachment to Y.

In certain embodiments, L is D-Ar—NR$^2$C(=O). Exemplary embodiments include the structures

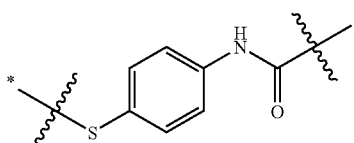

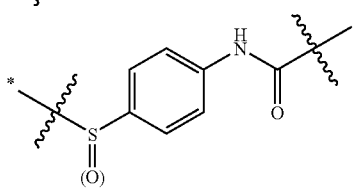

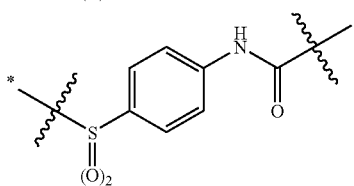

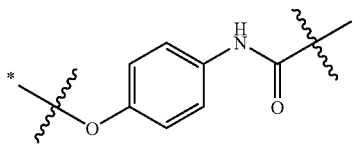

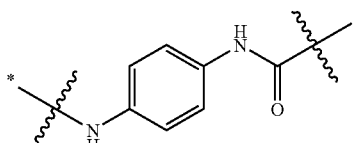

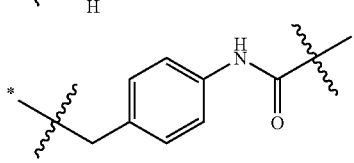

wherein the asterisk indicates the point of attachment to Y.

In certain embodiments, L is —OArC(=O)CH$_2$—. An exemplary embodiment includes the structure

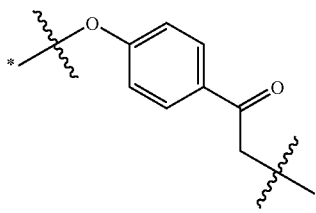

wherein the asterisk indicates the point of attachment to Y.

In certain embodiments, L is —S-Z-NHC(=O)—. An exemplary embodiment includes the structure

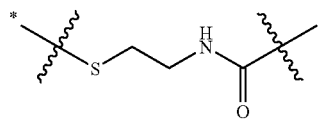

wherein the asterisk indicates the point of attachment to Y.

In certain embodiments, X is an optionally substituted alkyl or alkenyl. For example, in certain embodiments X is optionally substituted ethyl, propyl or allyl. Exemplary embodiments of optionally substituted allyl groups include, but are not limited to, the structures:

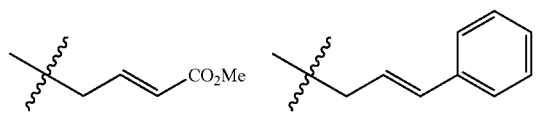
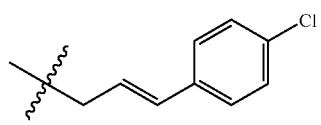
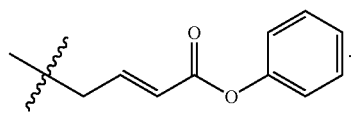

Examples of compounds of the present invention, include, but are not limited to, those shown in Scheme 1.

Scheme 1

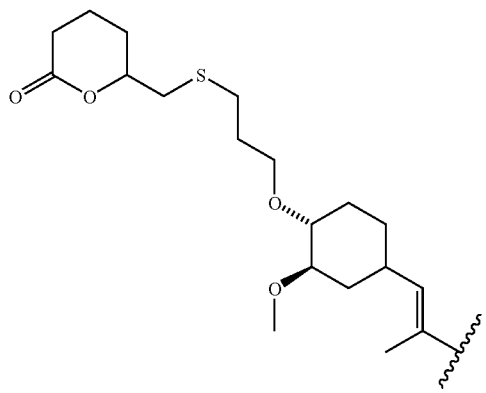

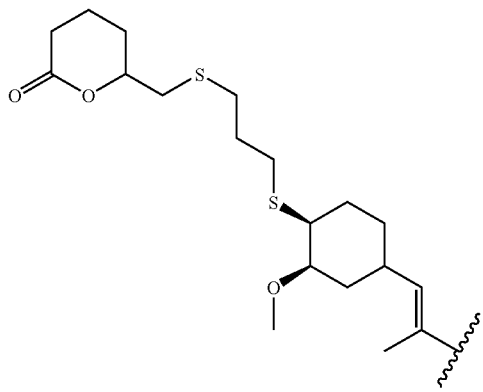
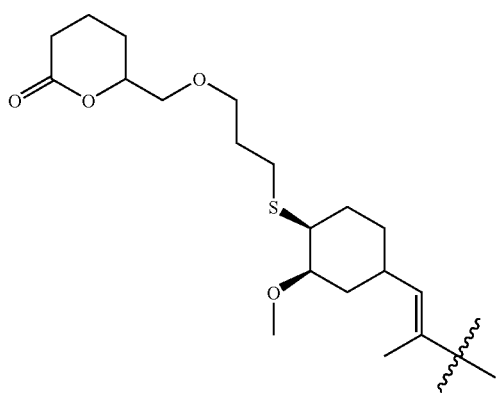
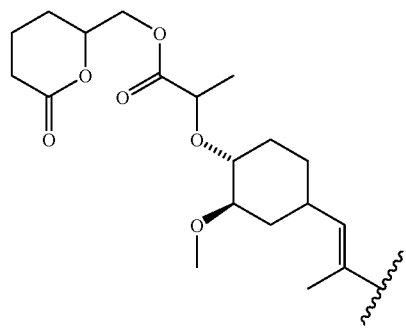
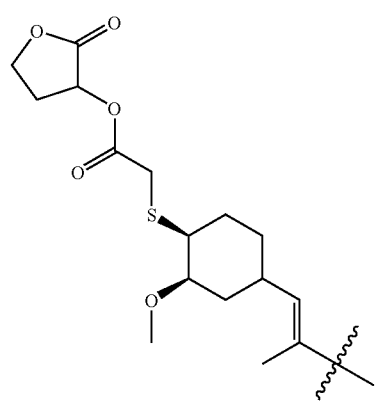
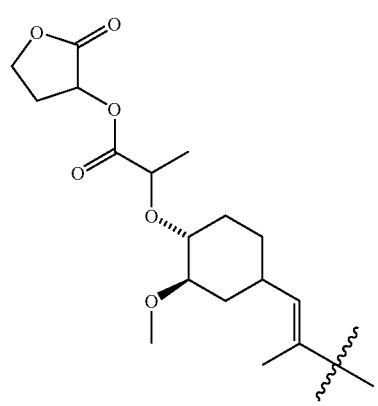
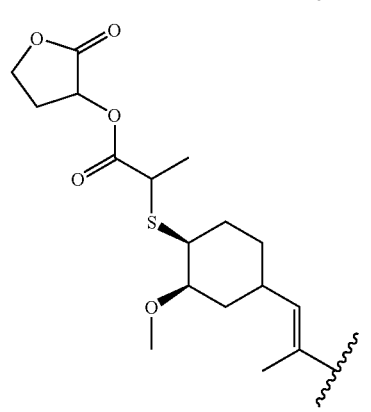

-continued
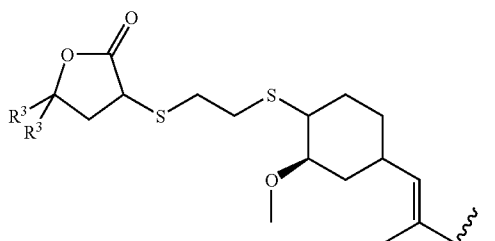
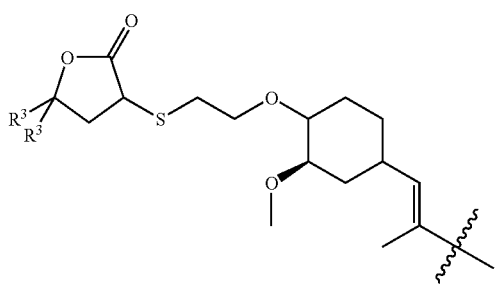
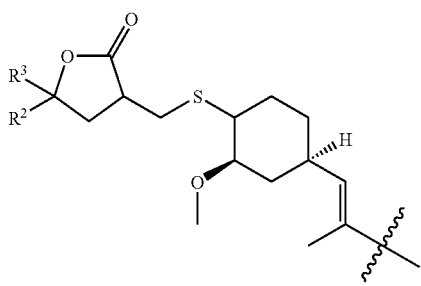
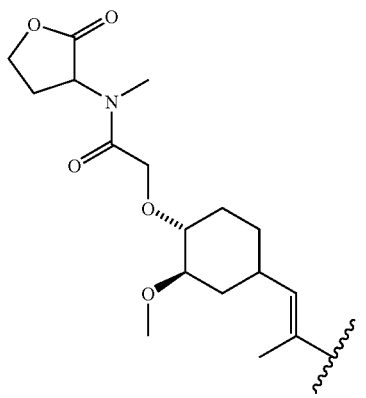
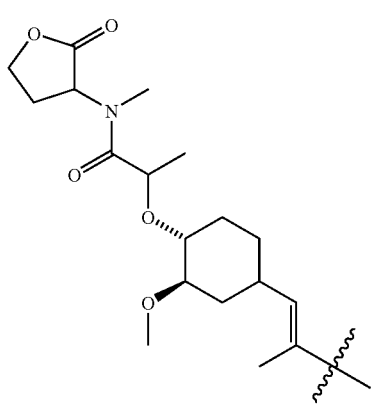
-continued
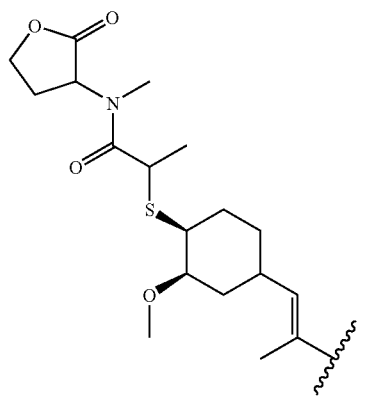
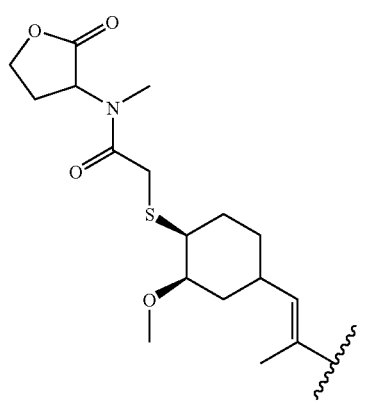
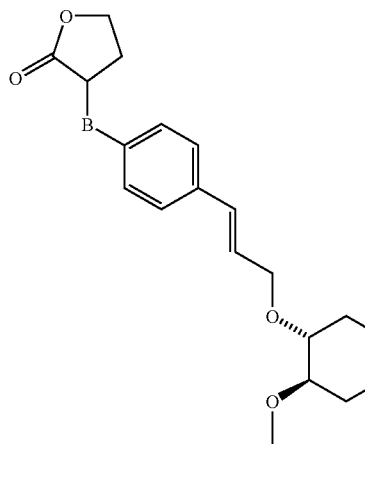

-continued
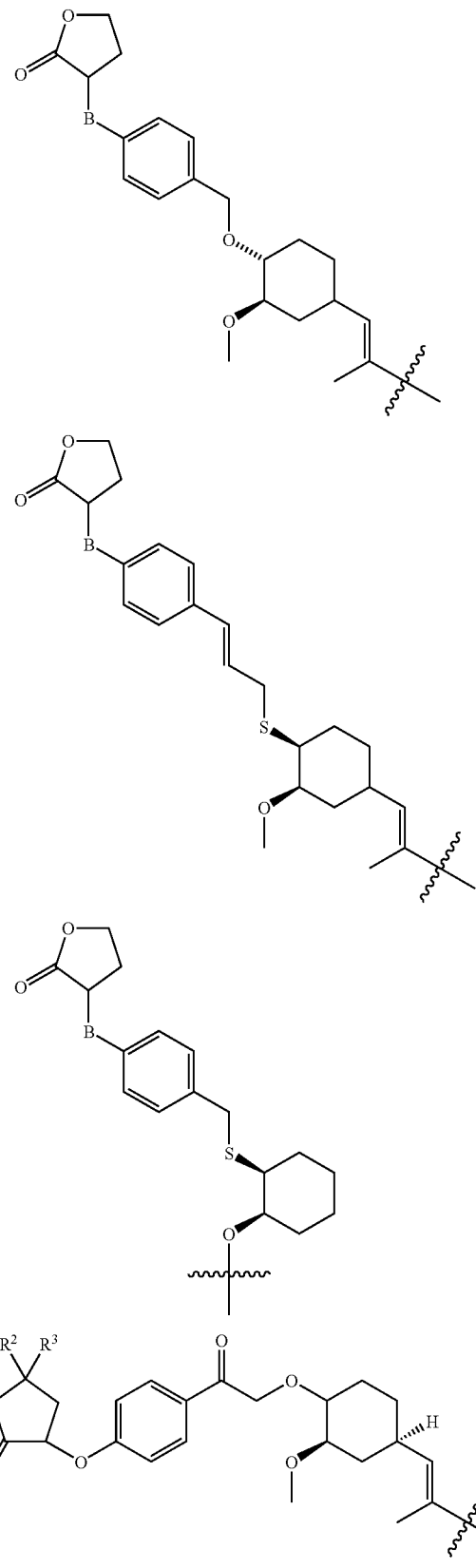
-continued
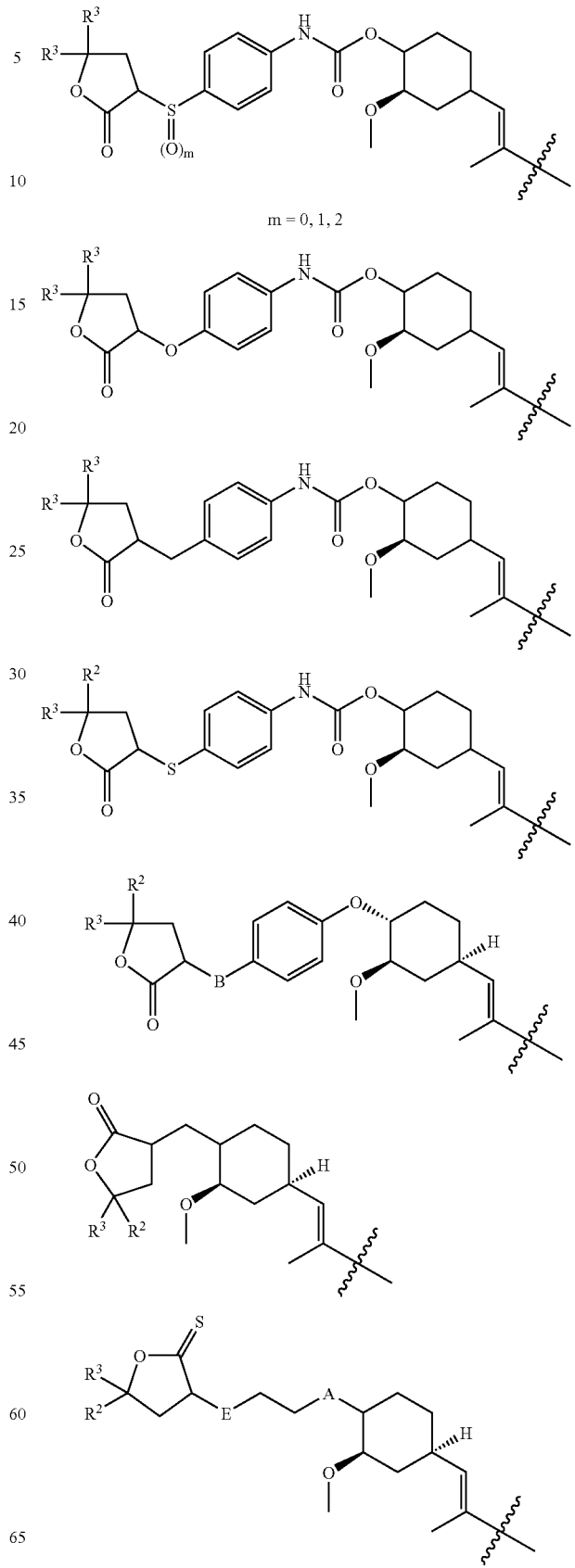
m = 0, 1, 2

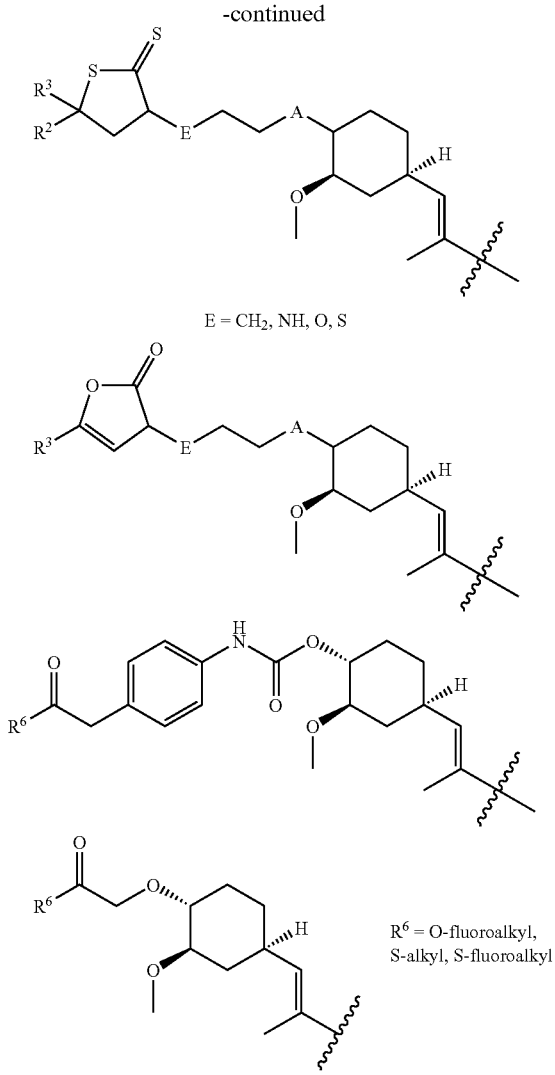

E = CH$_2$, NH, O, S

R$^6$ = O-fluoroalkyl, S-alkyl, S-fluoroalkyl

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and pure enantiomers of the Formula I. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

This invention also encompasses pharmaceutical compositions containing a compound of Formula I and methods of treating immunoregulatory or respiratory diseases, disorders and conditions, by administering compounds of the present invention.

In addition, the invention also includes solvates, pharmaceutically active metabolites, and pharmaceutically acceptable salts of compounds of Formula I.

The term "solvate" refers to an aggregate of a molecule with one or more solvent molecules.

A "pharmaceutically active metabolite" is a pharmacologically active product produced through metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}$C or $^3$H) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the pyrazolyl compounds of the invention.

A "pharmaceutically acceptable salt" as used herein, unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

Synthesis of Compounds of Formula I

The inventive compounds may be prepared using the reaction routes and synthesis schemes as described below, employing the techniques available in the art using starting materials that are readily available or can be synthesized using methods known in the art.

For illustrative purposes, Schemes 2-3 show general methods for preparing certain compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Scheme 2

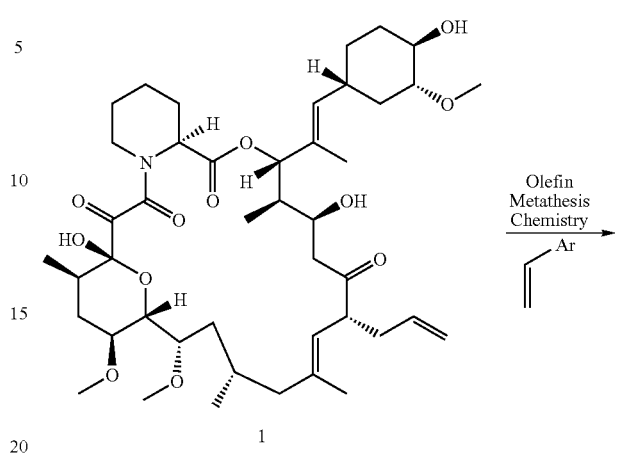

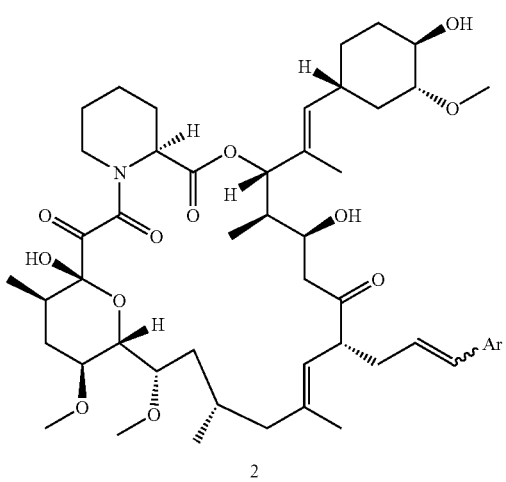

Scheme 2 shows a method of coupling an "X" group to a compound of Formula I, wherein X is an optionally substituted alkenyl group. As shown in Scheme 2, an olefin $CH_2$=CH—Ar is coupled a macrocyclic core (1) via standard olefin metathesis chemistry known to those skilled in the art to provide the coupled compound (2). An example olefin metathesis chemistry conditions includes heating the reagents with Nolan's catalyst and LiBr in a suitable solvent system such as THF and methylene chloride. Examples of suitable Ar groups for the $CH_2$=CH=Ar reagent include, but are not limited to, phenyl, 2-methylphenyl, 4-fluorophenyl, 4-trifluoromethylphenyl, 2-methoxyphenyl, 4-methoxyphenyl, 3-4-dimethoxyphenyl, 2-chlorophenyl, 3-chlorophenyl, 4-chlorophenyl, 3-bromophenyl, 4-bromophenyl, 3-($CO_2$Me)phenyl, 2-naphthyl, 3-t-butylphenyl, pentafluorophenyl, 4-$CH_3CO_2$-phenyl, 2,5-dimethylphenyl, pyridyl, pyrrolyl, thiophenyl, and oxazolyl.

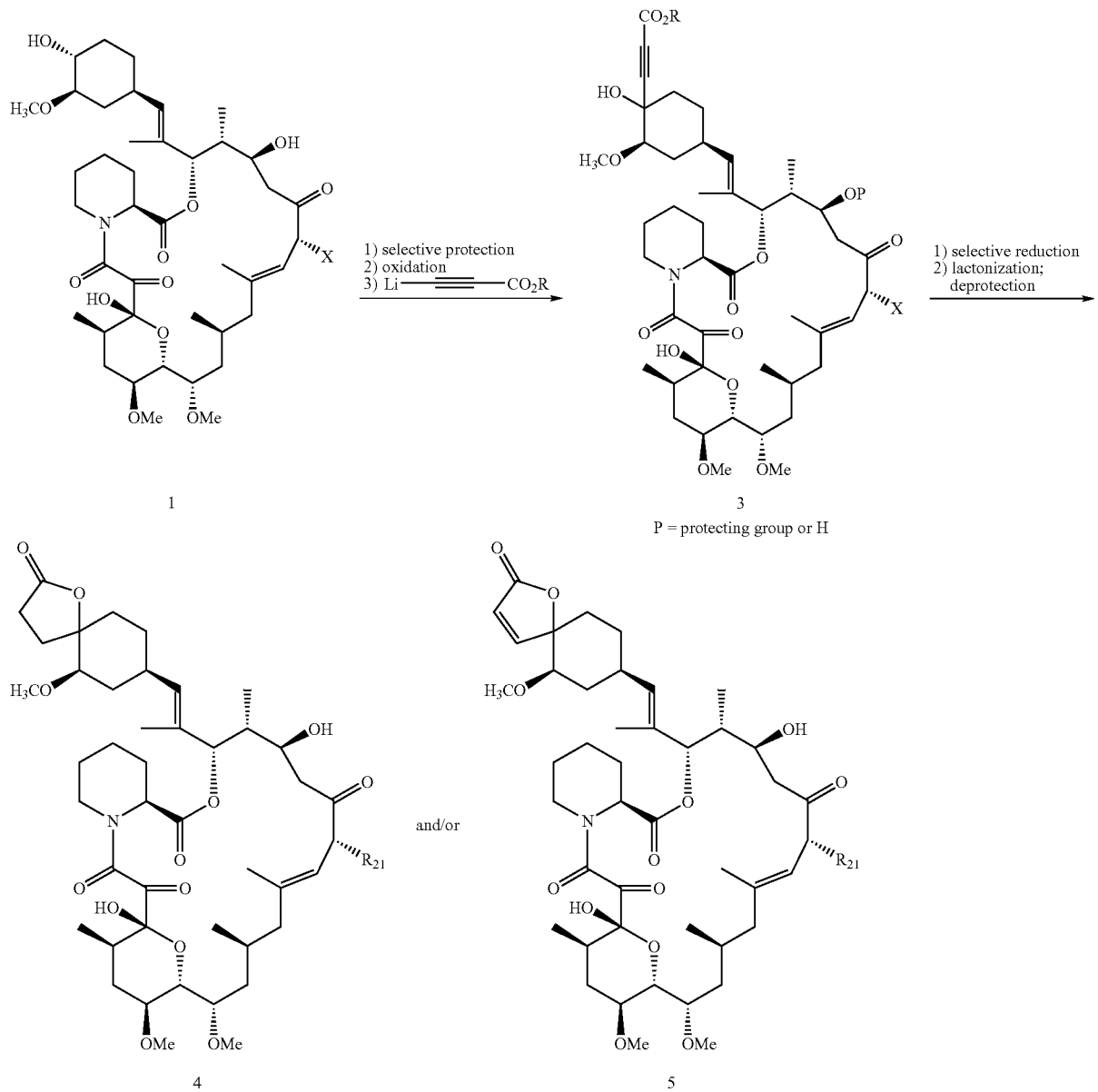

Scheme 3

P = protecting group or H

Scheme 3 shows a method of incorporating a Y-L-A moiety on a macrocyclic ring, wherein L and Y are absent and A represents a carbon atom and an oxygen atom each bonded to carbon 32 of the macrocyclic core. Accordingly to Scheme 3, the OH group on carbon 24 of compound (1) is selectively protected, and OH group at carbon 32 of the protected compound is oxidized. Subsequent treatment with a lithiated acetylene having the formula Li—C≡C—$CO_2R$, provides compound (3). Selective reduction of compound (3), followed by lactonization and deprotection provides compound (4) or compound (5) or a mixture of both.

Methods of Treatment with Compounds of Formula I

Compounds of Formula I show topical activity similar to cyclosporin and FK506, and therefore the compounds of this invention are clinically useful for the treatment of diseases or conditions responsive to, or requiring anti-inflammatory, immunosuppressive, or related therapy. For example, the compounds of this invention are useful in topical administration for the treatment of diseases or conditions of the eye, nasal passages, buccal cavity, colon, skin, intestinal tract, airway, or lung. In particular, the compounds of this invention permit topical anti-inflammatory, immunosuppressive or related therapy with the concomitant avoidance or reduction of undesirable systemic side effects, (e.g. general systemic immunosuppression).

Accordingly, this invention provides a method of treating diseases of conditions responsive to, or requiring anti-inflammatory, immunosuppressive, or related therapy, comprising administering a therapeutically effective amount of a compound of Formula I, or a diastereomer, tautomer, solvate, metabolite, or pharmaceutically acceptable salt thereof to a mammal in need of such treatment, wherein said compound is administered topically, via inhalation, ocularly, orally or rectally.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The terms "treating", "treat", and "treatment" embrace both preventative, i.e., prophylactic, and palliative treatment.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the inhibition of calcineurin, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

Compounds of Formula I are useful for the treatment of diseases or conditions having an autoimmune or inflammatory component and for which topical therapies may be practiced. Examples include treatments of the eye such as conjunctivitis, keratoconjunctivitis sicca, and vernal conjunctivitis and maintenance of corneal transplant, diseases affecting the nose including allergic rhinitis, as well as diseases of the colon, (e.g., Crohn's disease and ulcerative colitis), and for intestinal disorders and diseases, (e.g. celiac disease).

Compounds of Formula I are useful for the treatment by inhalation of diseases and conditions of the airways or lung, in particular inflammatory or obstructive airway disease. They are especially useful for the treatment of diseases or conditions of the airways or lung associated with or characterized by inflammatory cell infiltration or other inflammatory event accompanied by inflammatory cell (e.g., eosinophil and/or neutrophil) accumulation.

Compounds of Formula I are useful for the treatment of asthma of whatever type or genesis including both intrinsic and extrinsic asthma. Compounds of Formula I are useful for the treatment of atopic or non-atopic asthma, exercise-induced asthma, bronchitic asthma, including allergic asthma, occupational asthma, asthma induced following bacterial infection, and other non-allergic asthma. Treatment of asthma is to be understood as embracing treatment of "wheezy-infant syndrome". This is treatment of subject, (usually less than 4 or 5 years of age), exhibiting wheezing symptoms, particularly at night, and diagnosed or diagnosable as "wheezy infants". This is an established patient category of major medical concern and now more correctly identified as incipient or early-phase asthmatics. Compounds of Formula I are useful for the treatment of asthma patients whose asthmatic status is either steroid dependent or steroid resistant.

Compounds of Formula I are also useful for the treatment of bronchitis or for the treatment of chronic or acute airway obstruction associated therewith. Compounds of Formula I may be used for the treatment of bronchitis of whatever type of genesis, including, for example, acute bronchitis, arachidic bronchitis, catarrhal bronchitis, chronic bronchitis, croupous bronchitis, phthinoid bronchitis and so forth.

Compounds of Formula I are useful for the treatment of pneumoconiosis (an inflammatory, commonly occupational, disease of the lungs, frequently accompanied by airway obstruction, whether chronic or acute, and occasioned by repeated inhalation of dusts) of whatever type or genesis, including, for example, aluminosis, anthracosis, asbestosis, berylliosis, chalicosis, ptilosis, siderosis, silicosis, tabacosis, and in particular, byssinosis.

Compounds of Formula I may be used for the treatment of eosinophil-related disorders of the airway including hyper-eosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, and eosinophil-related disorders affecting the airways occasioned by drug reaction.

Compounds of Formula I may also be used to treat any condition of the airways or lung requiring immunosuppressive therapy. Examples include the treatment of autoimmune disease of, or as they affect, the lungs or for the maintenance of allogenic lung transplant (e.g., following lung or heart transplantation).

By provision of the analogs of the invention which are topically active, but systemically inactive, the present invention makes potent immunosuppressant therapy available to subjects for whom such therapy might otherwise be excluded due to the unacceptable risk of systemic side effect(s).

Another aspect of this invention provides a compound of this invention for use as a medicament in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Administration of Compounds of Formula I

In order to use a compound of the Formula I or a pharmaceutically acceptable salt thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt thereof, as defined hereinbefore in association with a pharmaceutically acceptable diluent or carrier.

To prepare the pharmaceutical compositions according to this invention, a therapeutically or prophylactically effective amount of a compound of Formula I or a pharmaceutically acceptable salt, solvate, or metabolite thereof (alone or together with an additional therapeutic agent) is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I, its use in the therapeutic compositions and preparations is contemplated. Supplementary active ingredients can also be incorporated into the compositions and preparations as described herein.

A compound of Formula I or pharmaceutically acceptable salt, solvate, or metabolite thereof may be administered by routes including, but not limited to, the pulmonary route (inhalation), nasal administration, rectal administration (e.g., suppository or enema form), dermally (topically to the skin), or orally. When administrated, the analogs of the invention will have potent efficacy at the site(s) of administration, while devoid of, or exhibit relatively reduced, systemic activity.

For example, a compound of Formula I or pharmaceutically acceptable salt, solvate, or metabolite thereof may be administered dermally, (i.e., topically to the skin), for example for the treatment of cutaneous diseases mediated by immune mechanisms, e.g., psoriasis, contact dermatitis, atopic dermatitis, alopecia areata, erythema multiforma, dermatitis, herpetiformis, scleroderma, vitiligo, hypersensitivity angiitis, urticaria, bullous pemphigoid, lupus, erythematosus, pemphisus, epidermolysis bullosa acquisita, and other inflammatory or allergic conditions of the skin. Optionally, the analogs of the invention are co-administered together with anti-inflammatory, immunosuppressive, or other pharmacologically active agents, (e.g., corticosteroids, antihistamines, antibiotics, antifungals, etc).

In other certain embodiments, a compound of Formula I or pharmaceutically acceptable salt, solvate, or metabolite thereof can be administered topically within the airways, e.g. by the pulmonary route, by inhalation. While having potent efficacy when administered topically, analogs of the invention are devoid of, or exhibit relatively reduced, systemic activity, e.g. following oral administration. Analogs of the invention thus provide a means for the treatment of diseases and conditions of the airways or lung with the avoidance of unwanted systemic side effect, e.g., consequent to inadvertent swallowing of drug substance during inhalation therapy.

Administration of a compound of Formula I or pharmaceutically acceptable salt, solvate, or metabolite thereof may also involve the use of controlled-release oral dosage forms that comprise a tablet or capsule containing a plurality of particles of a solid-state drug dispersed in a swellable/erodible polymer may be used. Further controlled release oral dosage forms of the analogs of the invention may be used for continuous, sustained administration to the upper gastrointestinal tract of a patient. The majority of the dose of analogs of the invention may be delivered, on an extended release basis, to the stomach, duodenum, and upper regions of the small intestine, with delivery of the drug to the lower gastrointestinal tract and colon substantially restricted. A variety of technologies, including hydrophilic, water-swellable, crosslinked, polymers that maintain physical integrity over the dosage lifetime but thereafter rapidly dissolve may be utilized for delivery of the analogs of the invention.

Pharmaceutical Formulations

In one aspect of this invention, a compound of Formula I or pharmaceutically acceptable salt, solvate, or metabolite thereof may be formulated into pharmaceutical compositions for administration to animals or humans to treat or prevent an immunoregulatory or respiratory disease, disorder, or condition. In order to use a compound of the Formula I, it can be formulated in accordance with standard pharmaceutical practice as a pharmaceutical composition. According to this aspect of the invention there is provided a pharmaceutical composition that comprises a compound of Formula I or pharmaceutically acceptable salt, solvate, or metabolite thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I will naturally vary according to the nature and severity of the conditions, the age and sex of the animal or patient and the route of administration, according to well known principles of medicine.

Representative compounds of the present invention, which are encompassed by the present invention include, but are not limited to the compounds of the examples and their pharmaceutically acceptable acid or base addition salts or solvates thereof. The examples presented below are intended to illustrate particular embodiments of the invention, and are not intended to limit the scope of the specification or the claims in any way.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as $CDCl_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

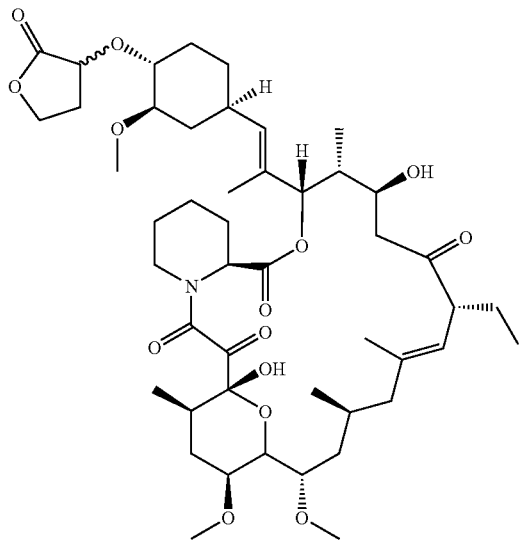

Step A: Preparation of 3-diazodihydrofuran-2-one: To a cooled (−78° C.) solution of dihydrofuran-2-one (500 mg, 5.8 mmol) in THF (10 mL) was added LiHMDS (6 mL, 6.0 mmol). After stirring for 45 minutes, trifluoroethyltrifluoroacetate (1.25 g, 6.4 mmol) was added and the mixture stirred for 10 minutes. The reaction mixture was poured into ether (10 mL) and 5% HCl (20 mL). The layers were separated and the aqueous layer was washed with ether. The combined organics were washed with saturated NaCl, dried over $Na_2SO_4$ and concentrated under reduced pressure. The residue was dissolved in acetonitrile (6 mL) and treated dropwise sequentially with water (0.104 mL), triethylamine (0.88 g, 7.2 mmol) and a solution of 4-dodecylbenzenesulfonyl azide (3.06 g, 8.7 mmol) dissolved in acetonitrile (4 mL). After stirring at room temperature for 16 hours, the reaction mixture was poured into ether/5% $Na_2CO_3$. The layers were separated and the aqueous layer was extracted with ether. The combined organics were washed with 5% $Na_2CO_3$ (4×), water (3×), saturated NaCl, dried over $Na_2SO_4$ and concentrated under reduced pressure. The residue was chromatographed (hexanes/EtOAc) to provide the product (85 mg, 13%).

Step B: Preparation of the 2-oxotetrahydro-furan-3-yloxy analog of FK520: To a solution of FK520 (20 mg, 0.025 mmol) in dichloromethane (1 mL) was added rhodium (II) acetate (<1 mg). After heating to reflux, a solution of 3-diazodihydrofuran-2-one (8 mg, 0.075 mmol) in dichloromethane (0.5 mL) was added dropwise to the reaction mixture. After heating at reflux for 30 minutes, the mixture was cooled to room temperature and stirred for 12 hours. The mixture was concentrated under reduced pressure and the residue was chromatographed (5:2 hexanes/acetone) to provide the desired product (10 mg, 46%) as colorless film. MS (ESI+) m/z 898 (M+Na) detected.

Example 2

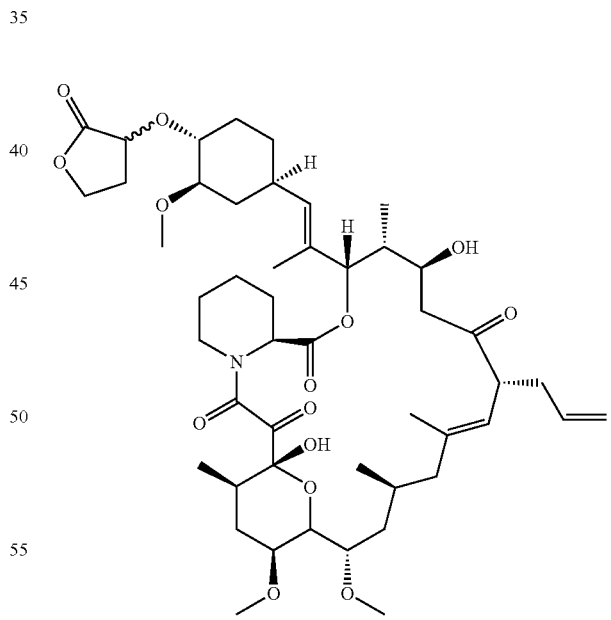

The 2-oxotetrahydrofuran-3-yloxy analog of FK506 was prepared from FK506 according to the procedure of Example 1 to provide the product in 66% yield. A portion of the product (75 mg) was rechromatographed (5:2 hexanes/EtOAc) and converted to foam by concentrating under reduced pressure form ether. MS (ESI+) m/z 911 (M+Na) detected.

Example 3

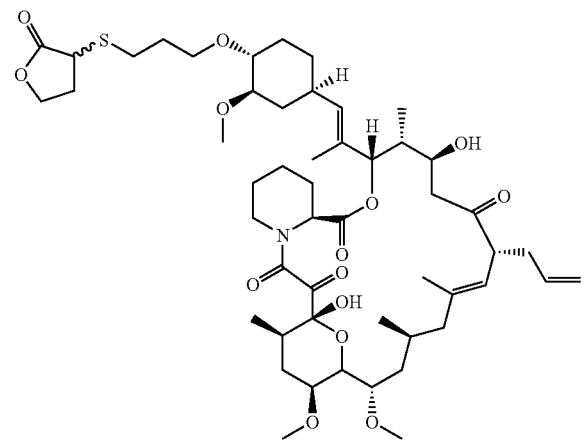

Step A: Preparation of 3-(3-hydroxypropylsulfanyl)-dihydrofuran-2-one: 3-Mercaptopropan-1-ol (1.61 g, 17.4 mmol) was dissolved in acetone (40 mL) followed by addition of cesium carbonate (5.67 g, 17.4 mmol) and 3-bromo-dihydrofuran-2(3H)-one (1.63 ml, 17.4 mmol). The suspension was stirred vigorously for 40 hours. The reaction was filtered through silica gel, rinsed with acetone and concentrated in vacuo. The residue was chromatographed on silica gel eluting with 70-80% ethyl acetate/hexanes. Recovered the desired product as an oil (2.1 g, 71%).

Step B: Preparation of the 3-(2-oxotetrahydrofuran-3-ylthio)propyl trifluoromethanesulfonate: Triflic anhydride (0.544 ml, 3.23 mmol) was added to a pre-cooled (0° C.) solution of 2,6-di-tert-butylpyridine (1.61 ml, 7.15 mmol) in methylene chloride (16 mL). A solution of 3-(3-hydroxypropylthio)-dihydrofuran-2(3H)-one (0.600 g, 3.41 mmol) dissolved in methylene chloride (2.5 mL) was added dropwise. The reaction was stirred at 0° C. for 15 minutes. The product was utilized in the subsequent step without isolation.

Step C: Preparation of 3-(2-oxotetrahydro-furan-3-ylsulfanyl)-propoxy analog of FK506: FK506 (0.2736 g, 0.3403 mmol) was added as a solid to the in situ generated triflate from Step B and the reaction was stirred at 0° C. for 46 hours. Lutidine (0.395 ml, 3.40 mmol) was added to consume any remaining triflate and the reaction was allowed to warm to ambient temperature then stirred for 1 hour. The reaction mixture was poured into 10% $KHSO_4$, separated, washed once with 10% $KHSO_4$, twice with water, dried over $Na_2SO_4$ and concentrated in vacuo. The residue was chromatographed on silica gel, eluting with 23% acetone/hexanes. The product was recovered as a foam, (0.20 g, 62%). MS (ESI+) m/z 984 (M+Na) detected.

Example 4

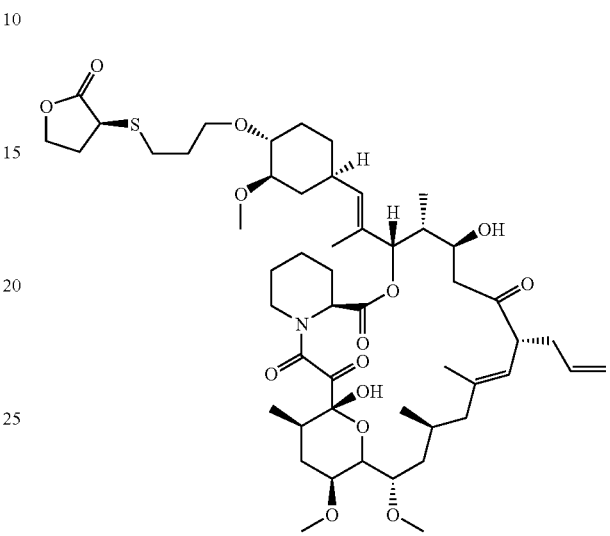

Step A: Preparation of (R)-toluene-4-sulfonic acid 2-oxotetrahydrofuran-3-yl ester: (R)-(−)-α-Hydroxy-γ-butyrolactone (1.61 g, 15.8 mmol), DIEA (2.14 g, 16.6 mmol), and DMAP (0.385 g, 3.16 mmol) were combined in dichloromethane (30 mL) and cooled to 0° C. Tosyl chloride (3.16 g, 16.6 mmol) was added and the reaction mixture was stirred at 0° C. for 1 hour. After warming to room temperature and stirring for 16 hours, the mixture was washed with 1N HCl (2×), water (2×), saturated $NaHCO_3$, NaCl, dried over $Na_2SO_4$ and concentrated under reduced pressure. The residue was chromatographed (30% EtOAc in hexanes) to provide the product (2.21 g, 55%) as white solid.

Step B: Preparation of 3-(S)-(3-hydroxypropylsulfanyl)-dihydrofuran-2-one: A solution of 3-mercaptopropan-1-ol (360 mg, 3.90 mmol) in THF (8 mL) cooled to 0° C. was treated with 60% NaH (86 mg, 2.15 mmol). After warming to room temperature and stirring for 30 minutes, a solution of (R)-toluene-4-sulfonic acid 2-oxotetrahydrofuran-3-yl ester (500 mg, 1.95 mmol) in THF (2 mL) was added. After stirring at room temperature for 60 hours, the reaction mixture was quenched with saturated $NaHCO_3$ and diluted with EtOAc. The organic layer was washed with saturated $NH_4Cl$, saturated $NaHCO_3$, saturated NaCl, dried over $Na_2SO_4$ and concentrated under reduced pressure. The residue was chromatographed (2:1 EtOAc/hexanes) to provide the product as colorless oil (155 mg, 45%).

Step C: Preparation of trifluoromethanesulfonic acid 3-(S)-(2-oxotetrahydro-furan-3-ylsulfanyl)-propyl ester: Prepared according to the procedure of Example 3, Step B.

Step D: Preparation of the 3-(2-oxotetrahydrofuran-3-(S)-ylsulfanyl)-propoxy analog of FK506: Prepared according to the procedure of Example 3, Step C to provide the desired product (40 mg, 14%) as colorless film. MS (ESI+) m/z 984 (M+Na) detected.

Example 5

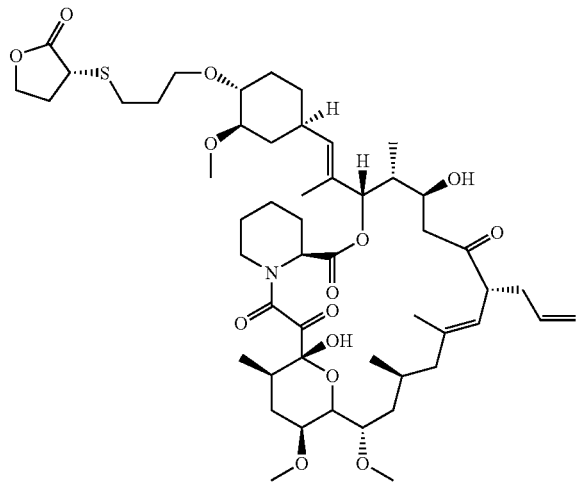

Prepared according to the procedure of Example 4, Steps A-D, from (S)-(+)-α-hydroxy-γ-butyrolactone to provide the desired product as colorless oil. MS (ESI+) m/z 984 (M+Na) detected.

Example 6

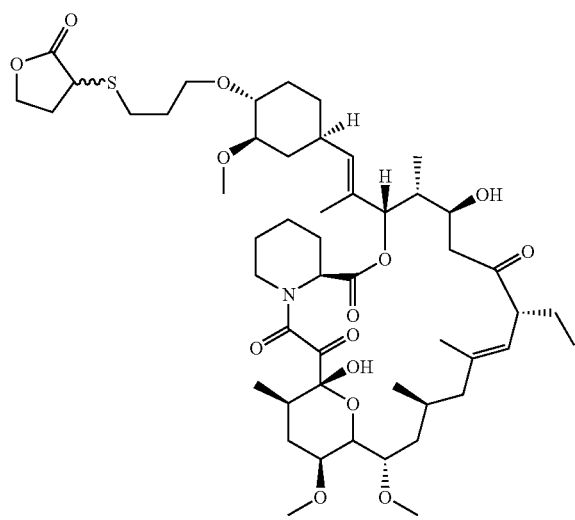

Prepared according to the procedure of Example 4, Steps A-D from FK520 and 2-hydroxy-γ-butyrolactone to provide the desired product as colorless film. MS (APCI−) m/z 949 (M−) detected.

Example 7

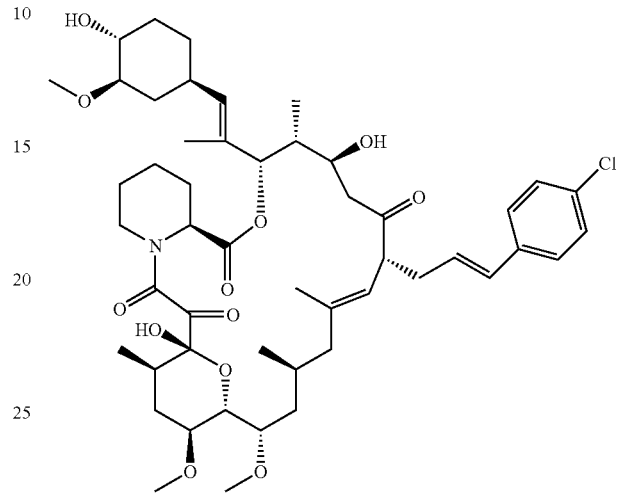

To a solution of FK506 (30 mg, 0.037 mmol) in DCM (0.75 mL) in a flame-dried flask under a $N_2$ atmosphere was added 1-chloro-4-vinylbenzene (52 mg, 0.37 mmol) and ruthenium [1,3-bis(2,4,6-trimethylphenyl)-2-imidazolidinylidene] dichloro[[2-(1-methylethoxy)phenyl]methylene] (2.3 mg, 0.0037 mmol). The resulting green solution was heated to reflux for 4 hours and then cooled to room temperature. The reaction mixture was chromatographed (0-4% MeOH in DCM) to provide the desired product (25 mg, 73%). MS (ESI+) m/z 936, 938 (M+Na, Cl pattern) detected.

Example 8

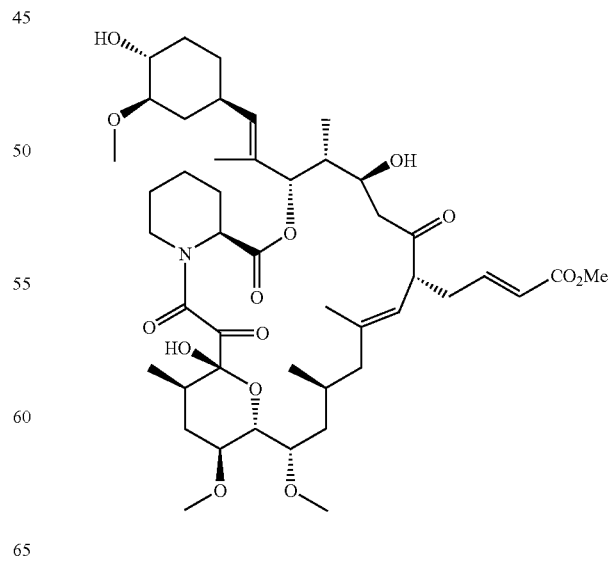

Prepared according to the procedure of Example 7 from FK506 and dimethyl maleate. The reaction mixture was chromatographed (25-40% acetone in hexanes) to provide the desired product (33 mg, 100%). MS (ESI+) m/z 884 (M+Na) detected.

Example 9

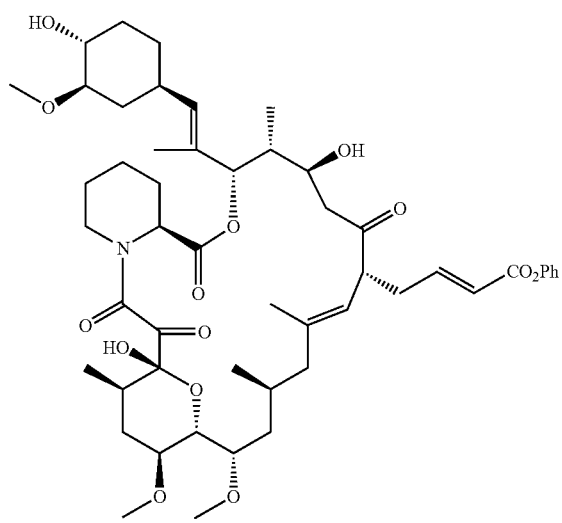

Prepared according to the procedure of Example 7 from FK506 and acrylic acid phenyl ester. The reaction mixture was chromatographed (20-35% acetone in hexanes) to provide the desired product (31 mg, 90%). MS (ESI+) m/z 946 (M+Na) detected.

Example 10

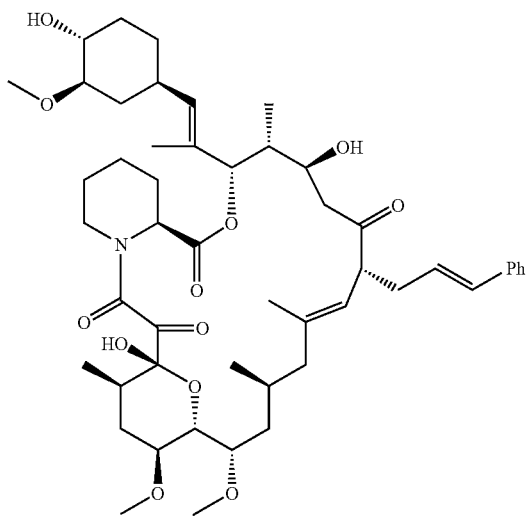

Prepared according to the procedure of Example 7 from FK506 and vinyl benzene. The reaction mixture was chromatographed (0-4% MeOH in DCM) to provide the desired product (25 mg, 76%). MS (ESI+) m/z 902 (M+Na) detected.

Example 11

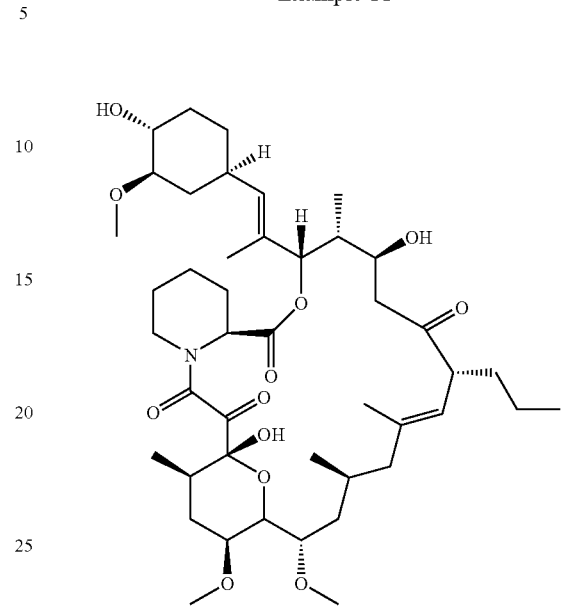

To a solution of FK506 (25 mg, 0.031 mmol) in 95% ethanol (0.2 mL) was added 10% Pd on carbon (1 mg). After stirring at room temperature under a hydrogen atmosphere for 1 hour, the mixture was filtered and concentrated under reduced pressure. The residue was chromatographed (2:1 hexanes/acetone) to provide the product (18 mg, 72%) as colorless oil. MS (ESI+) m/z 828 (M+Na) detected.

Example 12

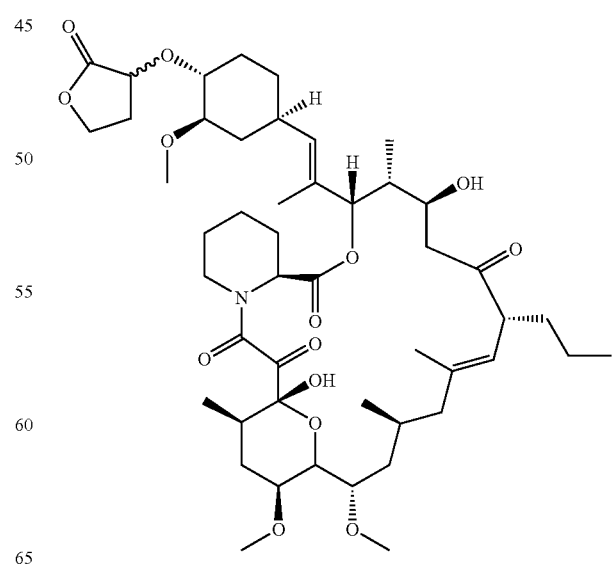

Prepared according to the procedure of Example 1 from the product of Example 11.

Example 13

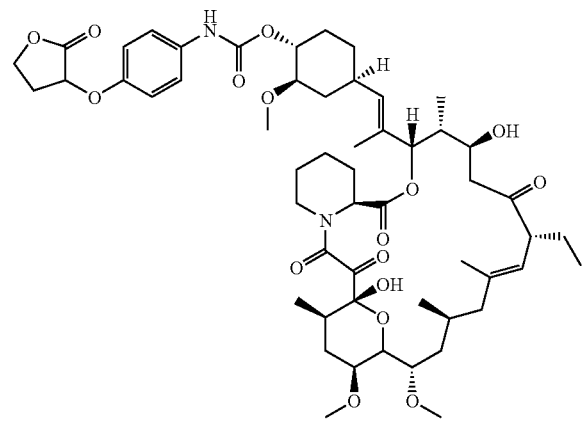

Step A: Preparation of 3-(4-nitrophenoxy)-dihydrofuran-2-one: To a solution of 4-nitrophenol (278 mg, 2.0 mmol) in DMF (6 mL) at room temperature under a nitrogen atmosphere was added powdered $K_2CO_3$ (552 mg, 2.0 mmol) followed by 3-bromo-dihydrofuran-2-one (330 mg, 2.0 mmol). After stirring at room temperature under a nitrogen atmosphere for 16 hours, the mixture was diluted to 30 mL with EtOAc and washed with water (4×30 mL) and brine (30 mL). The organic layer was dried over $MgSO_4$, filtered and concentrated under reduced pressure to provide the product (240 mg, 54%) as tan oil that later solidified.

Step B: Preparation of 3-(4-aminophenoxy)-dihydrofuran-2-one: To a solution of 3-(4-nitrophenoxy)-dihydrofuran-2-one (47 mg, 0.21 mmol) in EtOH (3 mL) was added palladium hydroxide (<1 mg). The reaction flask was evacuated and purged with $H_2$ and then stirred at room temperature under a $H_2$ atmosphere for 1 hour. The catalyst was removed by filtration and the filtrate was concentrated under reduced pressure to provide the desired product (40 mg, 99%).

Step C: Preparation of the [4-(2-oxotetrahydrofuran-3-yloxy)-phenyl]-carbamic acid analog of FK520: To a cooled (−78° C.) solution of FK520 (11.8 mg, 0.015 mmol) and DMAP (9.2 mg, 0.075 mmol) in DCM (75 µL) was added a solution of triphosgene (55 µL of a 0.1 M solution in DCM, 0.0055 mmol) dropwise. After stirring for 1 hour at −78° C., 3-(4-aminophenoxy)-dihydrofuran-2-one (100 µL of a 0.15 M solution in DCM, 0.015 mmol) was added. The reaction mixture was allowed to warm to room temperature and stirred for 1 hour. The mixture was diluted with ethyl acetate and saturated NaCl. The organic layer was washed with 1 N HCl and concentrated under reduced pressure. The residue was purified by reverse phase HPLC to provide the desired product (1.3 mg, 9%) as white solid. MS (ESI+) m/z 1028 (M+NH$_4$) detected.

Example 14

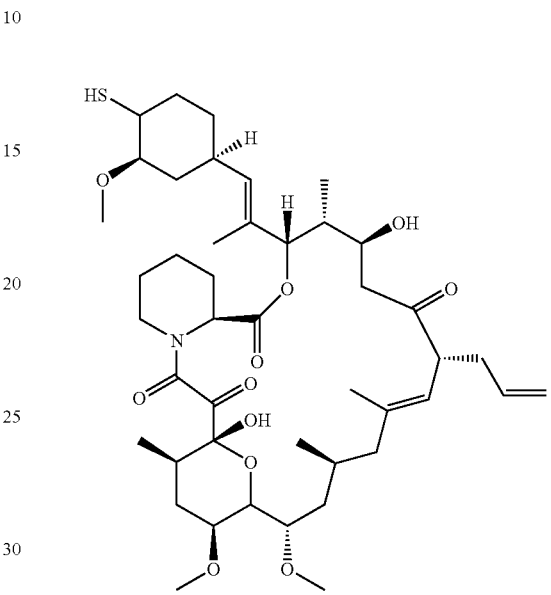

Step A: Preparation of C-32 triflate analog of FK506: FK506 (7.000 g, 8.706 mmol) was dissolved in methylene chloride (35 mL) and 2,6-dimethylpyridine (5.054 mL, 43.53 mmol) was added. The solution was cooled to −78° C. and triflic anhydride (3.662 mL, 21.77 mmol) was added slowly. The reaction was stirred at −78° C. for 2 hours. The reaction mixture was poured into ether and 10% $KHSO_4$, and the layers were separated. The organic layer was washed with 10% $KHSO_4$, water, and saturated sodium chloride, dried over $Na_2SO_4$ and concentrated in vacuo. A colorless oil was recovered, which was taken directly on to the subsequent step.

Step B: Preparation of C-32-thio analog of FK506: The crude triflate prepared in Step A (8.150 g, 8.707 mmol) was dissolved in THF (35 mL) and treated with 2,6-dimethylpyridine (1.617 mL, 13.93 mmol) and thiourea (0.7953 g, 10.45 mmol). The thiourea dissolved slowly over the first hour and the yellow solution was stirred at ambient temperature for 16 hours. Morpholine (1.523 mL, 17.41 mmol) was added and the reaction mixture was stirred at ambient temperature for 60 hours. The reaction mixture was diluted with ethyl acetate, then washed 3 times with 1N $KHSO_4$, once each with water, saturated $NaHCO_3$, water, and saturated NaCl. The combined organic layers were dried over $Na_2SO_4$ and concentrated in vacuo to recover a pale yellow film. The crude product was chromatographed on silica gel eluting with hexanes/acetone (5:1) and the product was recovered as a white solid (2.8 g, 39%). MS (ESI+) m/z 842 (M+Na) detected. Chiral normal phase HPLC showed that this product was an equal mixture of two diastereomers at C-32.

Example 15

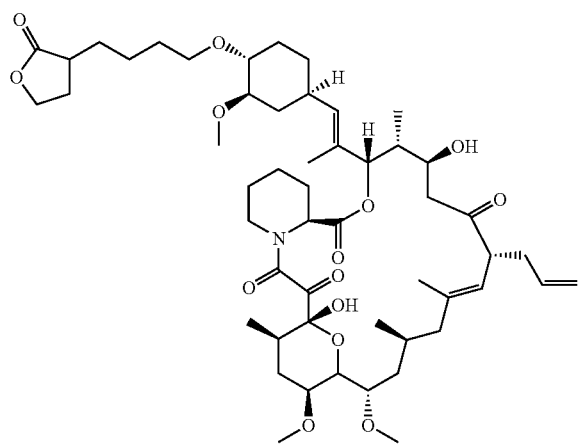

Step A: Preparation of 3-(4-hydroxybutyl)dihydrofuran-2 (3H)-one: To a mixture of 3-iodo-dihydrofuran-2(3H)-one (15.0 g, 70.8 mmol) and but-3-en-1-ol (12.2 mL, 142 mmol) in water (680 mL) under an argon atmosphere was added a 1 M solution of triethylborane in EtOH (7.1 mL, 7.1 mmol). The flask was then charged with air and the reaction was stirred at room temperature for 2 hours. Solid $NaHCO_3$ (35.7 g, 425 mmol) was added, followed by the careful addition of 50% hypophosphorous acid (39 mL, 360 mmol). After stirring at room temperature for 15 minutes, 2,2'-azobisisobutyronitrile (1.2 g, 7.1 mmol) was added and the reaction was heated to reflux for 1 hour. The reaction was cooled to room temperature, adjusted to pH=1 via the addition of 3% HCl, and then extracted three times with EtOAc. The organic layers were combined, dried over $MgSO_4$ and concentrated under reduced pressure. The crude product was chromatographed (2:1 EtOAc/hexanes) to provide the product as a colorless oil (3.7 g, 33%).

Step B: Preparation of 4-(2-oxotetrahydrofuran-3-yl)butyl trifluoromethanesulfonate: Trifluoromethanesulfonic anhydride (0.64 mL, 3.8 mmol) was added dropwise to a 0° C. solution of 3-(4-hydroxybutyl)-dihydrofuran-2(3H)-one (0.50 g, 3.2 mmol) and DIEA (0.94 mL, 5.4 mmol) in $CH_2Cl_2$ (15 mL). After stirring at 0° C. for 1.5 hours, the reaction was diluted with $CH_2Cl_2$ and washed sequentially with water, 1 M HCl, and water. The organics were dried over $MgSO_4$ and concentrated under reduced pressure. The crude product was chromatographed (1:2 EtOAc/hexanes) to afford the product as a colorless oil (0.21 g, 23%).

Step C: Preparation of the 4-(2-oxotetrahydrofuran-3-yl) butyl analog of FK506: FK506 (0.50 g, 0.63 mmol) was added to a 0° C. solution of 4-(2-oxo-tetrahydrofuran-3-yl) butyl trifluoromethanesulfonate (1.0 g, 3.4 mmol) and lutidine (1.2 mL, 10 mmol) in $CH_2Cl_2$ (2.5 mL). After stirring the reaction at room temperature for 1 hour, the solution was diluted with EtOAc and washed three times with 10% $KHSO_4$, twice with water, and once with saturated $NaHCO_3$. The organics were dried over $MgSO_4$ and concentrated under reduced pressure. The crude product was chromatographed (1:3 acetone/hexanes) to provide a foam enriched with the desired product. The product was further purified by normal-phase isocratic HPLC (EtOH/hexanes) to yield the pure title compound (26 mg, 4%). MS (ESI+) m/z 966 (M+Na) detected.

Example 16

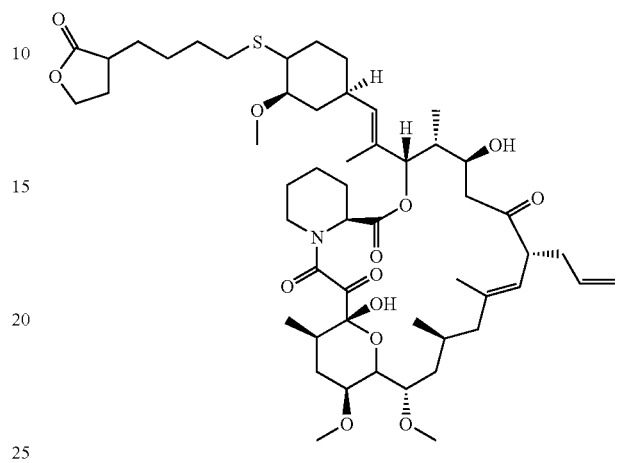

The 4-(2-oxotetrahydrofuran-3-yl)butyl analog of C32-thio-FK506 was prepared according to the procedure of Example 15, Step C from C32-thio-FK506 and 4-(2-oxotetrahydrofuran-3-yl)butyl trifluoromethanesulfonate, substituting DIEA for lutidine to provide the desired product (4 mg, 1.5%). MS (ESI+) m/z 984 (M+Na) detected.

Example 17

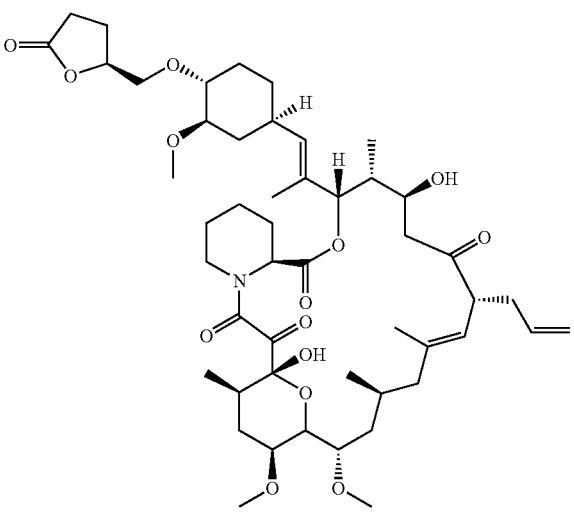

Step A: Preparation of (S)-(5-oxotetrahydrofuran-2-yl) methyl trifluoromethanesulfonate: Trifluoromethanesulfonic anhydride (0.97 g, 3.4 mmol) was added dropwise to a 0° C. solution of (S)-5-(hydroxymethyl)-dihydrofuran-2(3H)-one (0.20 g, 1.7 mmol) and lutidine (0.41 g, 3.8 mmol) in $CH_2Cl_2$ (2 mL). The reaction was stirred at 0° C. for 1.5 hours, then diluted with 1:4 EtOAc/hexanes and passed through a plug of silica gel. The volatiles were removed under reduced pressure to yield a yellow oil which was used immediately without purification (0.38 g, 89%).

Step B: Preparation of the (S)-(5-oxotetrahydrofuran-2-yl)methyl analog of FK506: FK506 (0.10 g, 0.12 mmol) was added all at once to a −10° C. solution of (S)-(5-oxotetrahydrofuran-2-yl)methyl trifluoromethanesulfonate (0.11 g, 0.44 mmol) and DIEA (0.13 mL, 0.75 mmol) in CH$_2$Cl$_2$. The reaction was allowed to warm to room temperature and was stirred overnight. The solution was diluted with CH$_2$Cl$_2$ and washed twice with 10% KHSO, once with water, and twice with 6% NaHCO$_3$. The organics were dried over MgSO$_4$ and concentrated under reduced pressure. The residue was chromatographed (1:19 acetone/hexanes) to provide a foam enriched with the desired product. The product was further purified by normal-phase isocratic HPLC (EtOH/hexanes) to yield the pure title compound (9 mg, 12%). MS (ESI+) m/z 924 (M+Na) detected.

Example 18

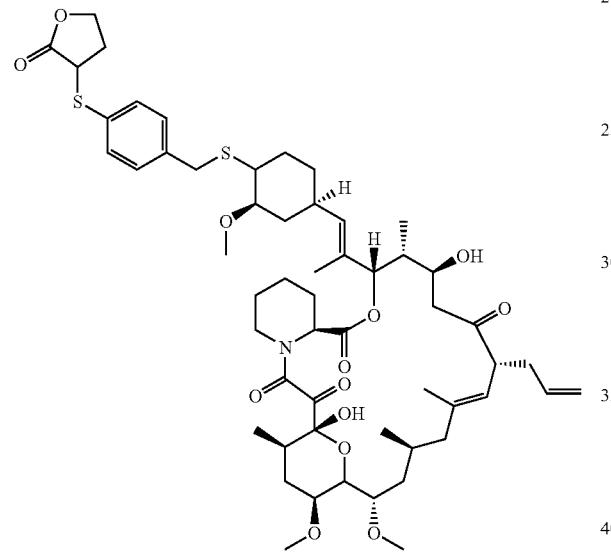

Step A: Preparation of 3-(4-(hydroxymethyl)phenylthio)dihydrofuran-2(3H)-one: 3-bromo-dihydrofuran-2(3H)-one (2.35 g, 14.3 mmol) was added to a solution of (4-mercaptophenyl)methanol (2.00 g, 14.0 mmol) and triethylamine (2.4 mmol, 17 mmol). The reaction was stirred at room temperature overnight, then was diluted with CH$_2$Cl$_2$ and washed sequentially with saturated NH$_4$Cl and NaCl solutions. The organics were dried over MgSO$_4$ and concentrated under reduced pressure to provide the product as a viscous oil (2.3 g, 72%).

Step B: Preparation of 4-(2-oxotetrahydrofuran-3-ylthio)benzyl 2,2,2-trichloroacetimidate: 1,8-Diazabicyclo[5.4.0]undec-7-ene (34 mg, 0.22 mmol) was added to a 0° C. solution of 3-(4-(hydroxymethyl)phenylthio)dihydrofuran-2(3H)-one (1.0 g, 4.5 mmol) and 2,2,2-trichloroacetonitrile (3.2 g, 22 mmol). The reaction was stirred for 1 hour, then directly chromatographed (3:7 ethyl acetate/hexanes) to provide the product as a viscous oil (1.6 g, 31%)

Step C: Preparation of the 4-(2-oxotetrahydrofuran-3-ylthio)benzyl analog of C32-thio-FK506: One drop of trifluoromethanesulfonic acid was added to a solution of C32-thio-FK506 (0.10 g, 0.12 mmol) and 4-(2-oxotetrahydrofuran-3-ylthio)benzyl 2,2,2-trichloroacetimidate (0.054 g, 1.4 mmol) in 1:1 CH$_2$Cl$_2$/cyclohexane (2 mL). After the reaction was stirred for 1 hour, 4-(2-oxotetrahydrofuran-3-ylthio)benzyl 2,2,2-trichloroacetimidate (0.11 g, 2.8 mmol) was added. The reaction was stirred for an additional 2 hours, then was quenched with triethylamine and chromatographed on silica gel (ethyl acetate) to provide a solid enriched in the desired product (40 mg). The product was further purified by normal-phase isocratic HPLC (EtOH/hexanes) to yield the pure title compound (3 mg, 2%). MS (ESI+) m/z 1048 (M+Na) detected.

Example 19

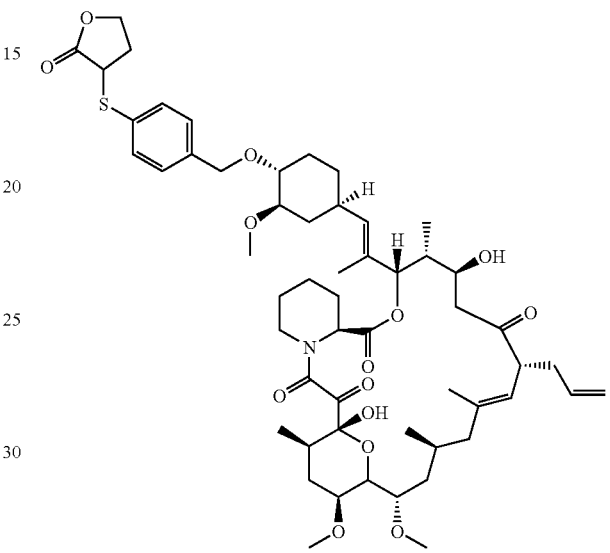

The (S)-4-(2-oxo-tetrahydrofuran-3-ylthio)benzyl analog of FK506 was prepared according to the procedure of Example 18, Step C from FK506 and 4-(2-oxotetrahydrofuran-3-ylthio)benzyl 2,2,2-trichloroacetimidate (6 mg, 5%). MS (ESI+) m/z 1032 (M+Na) detected.

Example 20

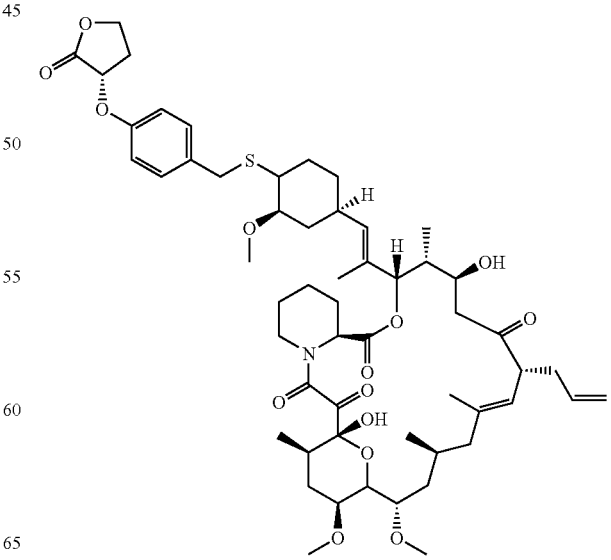

Step A: Preparation of 1-(tert-butyldimethylsilyloxy)-4-((tert-butyldimethylsilyloxy)methyl)benzene: A solution of 4-(hydroxymethyl)phenol (5.0 g, 40 mmol), imidazole (11 g, 160 mmol), and tert-butylchlorodimethylsilane (15 g, 100 mmol) in DMF (125 mL) was heated at 50° C. for 4 hours. The solution was cooled to room temperature and subsequently poured into water and extracted 3 times with diethyl ether. The combined organics were washed with brine, dried over MgSO$_4$, and concentrated under reduced pressure to provide the product as a colorless oil (14 g, 99%).

Step B: Preparation of 4-((tert-butyldimethylsilyloxy)methyl)phenol: Tetrabutylammonium fluoride (1 M THF, 44 mL, 44 mmol) was added to a 0° C. solution of 1-(tert-butyldimethylsilyloxy)-4-((tert-butyldimethylsilyloxy)methyl)benzene (14 g, 40 mmol) in THF (400 mL). The reaction was stirred for 30 minutes, then poured into a mixture of saturated NH$_4$Cl and Et$_2$O. The layers were separated and the aqueous phase was extracted twice with Et$_2$O. The organics were combined, washed with brine, dried over MgSO$_4$, and concentrated under reduced pressure. The residue was chromatographed (1:9 EtOAc/hexanes) to provide the product as a colorless oil (8.0 g, 85%).

Step C: Preparation (S)-3-(4-((tert-butyldimethylsilyloxy)methyl)phenoxy)-dihydrofuran-2(3H)-one: A solution of diethyl azodicarboxylate (40% toluene, 15 mL) was slowly added to a 0° C. solution of (R)-3-hydroxy-dihydrofuran-2(3H)-one, 4-((tert-butyldimethylsilyloxy)methyl)phenol, and triphenylphosphine. The reaction was stirred at room temperature overnight. The volatiles were removed under reduced pressure and the residue was taken up in diethyl ether and filtered. The filtrate was then successively washed with H$_2$O and brine. The organics were dried over MgSO$_4$ and concentrated under reduced pressure. The residue was chromatographed (1:4 ethyl acetate/hexanes) to provide the desired product (2.0 g, 29%).

Step D: Preparation of (S)-3-(4-(hydroxymethyl)phenoxy)-dihydrofuran-2(3H)-one: A solution of 40% aqueous hydrofluoric acid in CH$_3$CN (10 mL) was added to a 0° C. solution of (S)-3-(4-((tert-butyldimethylsilyloxy)methyl)phenoxy)-dihydrofuran-2(3H)-one in CH$_3$CN (50 mL). The reaction was stirred for 30 minutes and then partitioned between a saturated NaHCO$_3$ solution and diethyl ether. The organics were dried over MgSO$_4$ and concentrated under reduced pressure. The residue was chromatographed to provide the desired product (0.92 g, 72%).

Step E: Preparation of (S)-4-(2-oxo-tetrahydrofuran-3-yloxy)benzyl 2,2,2-trichloroacetimidate: Prepared according to the procedure of Example 18, Step B from (S)-3-(4-(hydroxymethyl)phenoxy)-dihydrofuran-2(3H)-one.

Step F: Preparation of the (S)-4-(2-oxo-tetrahydrofuran-3-yloxy)benzyl analog of thio-FK506: Prepared according to the procedure of Example 18, Step C from C32-thio-FK506 and (S)-4-(2-oxo-tetrahydrofuran-3-yloxy)benzyl 2,2,2-trichloroacetimidate (7 mg, 6%). MS (ESI+) m/z 1032 (M+Na) detected.

Example 21

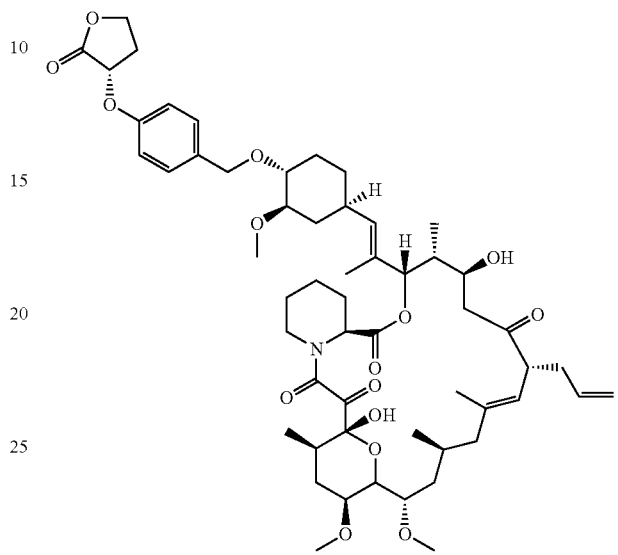

The (S)-4-(2-oxotetrahydrofuran-3-yloxy)benzyl analog of FK506 was prepared according to the procedure of Example 18, Step C from FK506 and (S)-4-(2-oxo-tetrahydrofuran-3-yloxy)benzyl 2,2,2-trichloroacetimidate without the HPLC purification step to provide a foam enriched with the desired compound (70 mg, 57%). MS (ESI+) m/z 1016 (M+Na) detected.

Example 22

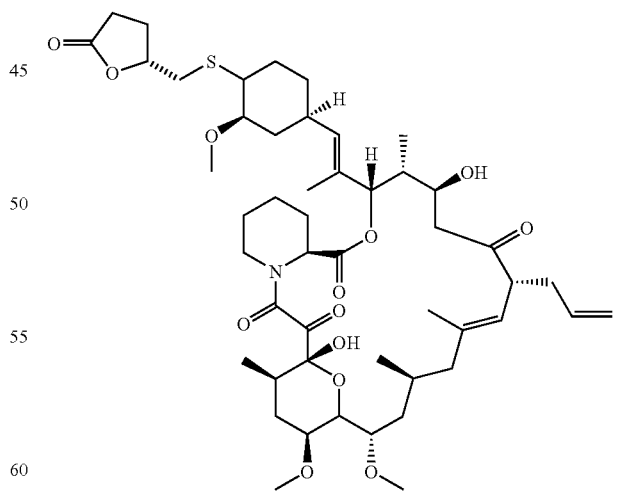

Step A: Preparation of (R)-(5-oxotetrahydrofuran-2-yl)methyl trifluoromethanesulfonate: Prepared according to procedure of Example 17, Step A from (R)-5-(hydroxymethyl)-dihydrofuran-2(3H)-one to provide the desired product as a colorless oil.

Step B: Preparation of the (R)-(5-oxotetrahydrofuran-2-yl)methyl analog of thio-FK506: Prepared according to the procedure of Example 17, Step B to yield the pure title compound (4 mg, 4%). MS (ESI+) m/z 940 (M+Na) detected.

Example 23

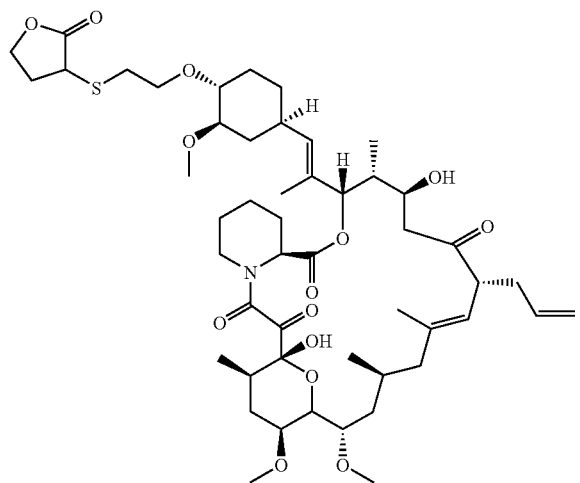

Preparation of the 3-(2-oxotetrahydrofuran-3-ylsulfanyl)-ethoxy analog of FK506: Prepared according to the procedure of Example 3, Steps A-C to yield a foam enriched with the title compound (6 mg, 3%). MS (ESI+) m/z 970 (M+Na) detected.

Example 24

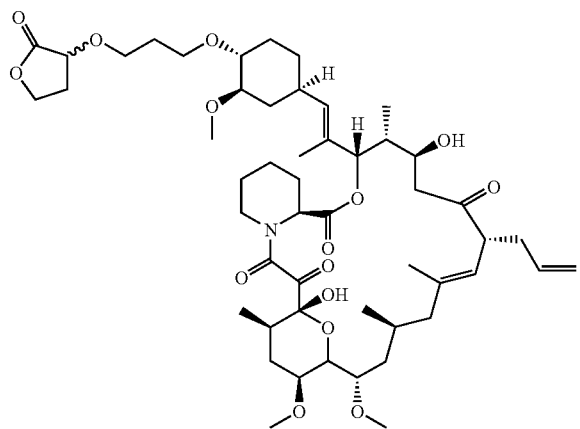

Step A: Preparation of 3-Diazodihydrofuran-2(3H)-one: Butyrolactone (2.50 g, 29.0 mmol) was dissolved in THF (50 mL), cooled to −78° C. and treated with LiHMDS (1.0 M in THF, 30.5 mL, 30.5 mmol). The reaction was stirred for 45 minutes then added trifluoroethyltrifluoroacetate (4.28 mL, 31.9 mmol) and stirred for 10 minutes. The reaction mixture was poured into ether (50 mL) and 5% HCl (100 mL). The layers were separated, the aqueous was washed 2 times with diethyl ether. The combined organics were washed with saturated NaCl, dried over $Na_2SO_4$ and concentrated in vacuo. The residue was immediately dissolved in acetonitrile (30 mL) and treated dropwise in sequence with water (0.52 mL), triethylamine (6.07 mL, 43.6 mmol) then with a solution of 4-dodecylbenzenesulfonyl azide (15.3 g, 43.6 mmol) dissolved in acetonitrile (20 mL). The mixture was stirred at ambient temperature for 16 hours. The reaction mixture was poured into diethyl ether/5% $Na_2CO_3$ and separated. The aqueous layer was washed with ether then the combined organics were washed 4 times with 5% $Na_2CO_3$, 3 times with water, once with saturated NaCl, dried over $Na_2SO_4$ then concentrated in vacuo to a yellow oil. The residue was chromatographed on silica gel using hexanes/ethyl acetate (3:2). After concentration in vacuo, 3-diazodihydrofuran-2(3H)-one was recovered as a yellow oil (1.27 g, 39%).

Step B: Preparation of 3-(3-Hydroxypropoxy)-dihydrofuran-2(3H)-one: Propane-1,3-diol (0.050 g, 0.657 mmol) was dissolved in dichloromethane (6.5 mL) and treated with rhodium (II) acetate (3 mg) then solution was heated to reflux. One third of a solution (ca. 2 mL) of 3-diazodihydrofuran-2(3H)-one (0.283 g, 0.986 mmol) dissolved in a mixture of dichloromethane (3 mL) and diethyl ether (2.5 mL) was added dropwise to the hot solution then the solution was heated at reflux for 30 minutes. The solution of 3-diazodihydrofuran-2(3H)-one was added in two portions (ca. 2 mL each) to the refluxing mixture in a similar manner. The reaction was cooled to ambient temperature and concentrated in vacuo. The crude oil was chromatographed on silica gel eluting with ethyl acetate/hexanes (2:1). 3-(3-Hydroxypropoxy)dihydrofuran-2(3H)-one was recovered as a colorless oil (47 mg, 45%).

Step C: Preparation of 3-(3-hydroxypropoxy)-dihydrofuran-2(3H)-one ether analog of FK506: 3-(3-Hydroxypropoxy)-dihydrofuran-2(3H)-one (0.043 g, 0.267 mmol) was dissolved in toluene (1 mL) and treated with 2,6-dimethylpyridine (0.124 mL, 1.07 mmol). The solution was cooled to −20° C. then treated with triflic anhydride (0.052 ml, 0.307 mmol). The mixture was stirred at −20° C. for 1 hour, then FK506 (0.0716 g, 0.0891 mmol) was added as a solid. The suspension was stirred at −20° C. and allowed to warm to ambient temperature with the bath. After 16 hours, the reaction mixture was concentrated with a stream of $N_2$ (g), resuspended in ethyl acetate then washed 3 times with 1N HCl, once with water, 3 times with saturated $NaHCO_3$, and once with saturated NaCl. The organic extracts were dried over $Na_2SO_4$ and concentrated in vacuo. The residue was chromatographed on silica gel eluting with 23% acetone/hexanes. The desired product was recovered as a white solid (8.7 mg, 10%). MS (ESI+) m/z 968 (M+Na) detected.

Example 25

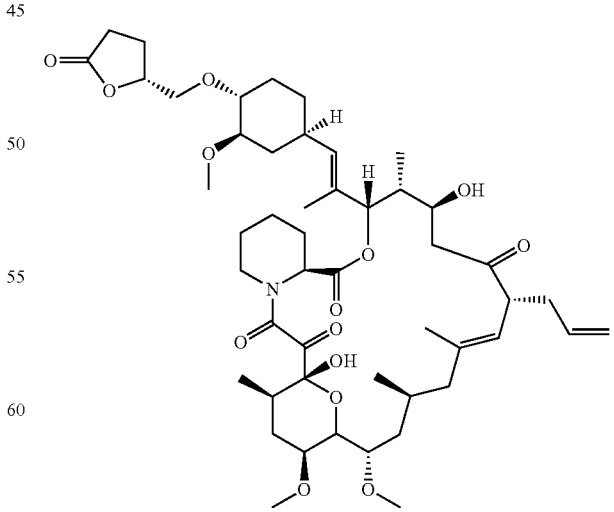

Step A: Preparation of (R)-(5-oxo-tetrahydrofuran-2-yl)methyl trifluoromethanesulfonate: (R)-5-(Hydroxymethyl)- dihydrofuran-2(3H)-one (0.500 g, 4.31 mmol) was dissolved in methylene chloride (10 mL), treated with 2,6-dimethylpyridine (1.50 ml, 12.9 mmol) then cooled to 0° C. Triflic anhydride (0.869 mL, 5.17 mmol) was added and the reaction mixture was stirred at 0° C. for 2 hours. The reaction mixture was poured into 10% $KHSO_4$ and separated. The organic layer was washed twice with 10% $KHSO_4$, once with water, 3 times with 6% $NaHCO_3$, then dried over $Na_2SO_4$ and concentrated in vacuo to provide (R)-(5-oxo-tetrahydrofuran-2-yl)methyl trifluoromethanesulfonate.

Step B: Preparation of (R)-5-(Hydroxymethyl)-dihydrofuran-2(3H)-one ether analog of FK506: (R)-(5-Oxo-tetrahydrofuran-2-yl)methyl trifluoromethanesulfonate (1.07 g, 4.31 mmol) was dissolved in toluene (4 mL), cooled to 0° C. then treated with 2,6-dimethylpyridine (0.500 mL, 4.31 mmol). FK506 (0.866 g, 1.08 mmol) was added to the solution as a solid. The reaction was stirred at 0° C. for 1 hour, then warmed to ambient temperature and stirred for 14 hours. The reaction mixture was concentrated with a stream of $N_2$ (g), resuspended in ethyl acetate then washed 3 times with 1N HCl, once with water, 3 times with saturated $NaHCO_3$, and once with saturated sodium chloride. The organic extracts were dried over $Na_2SO_4$ and concentrated in vacuo. The residue was chromatographed on silica gel eluting with 25% acetone/hexanes. The desired product was recovered as a colorless film (26 mg, 2.7%). MS (ESI+) m/z 924 (M+Na) detected.

Example 26

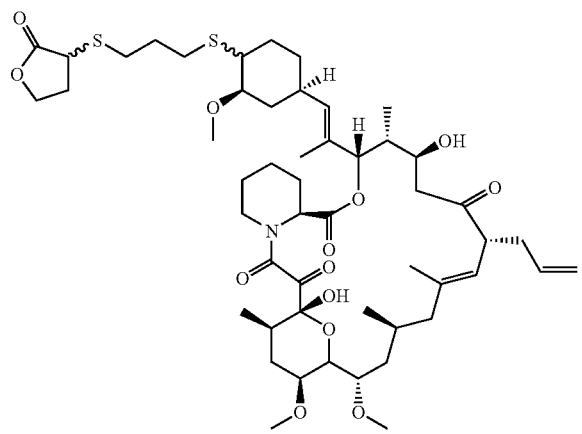

Step A: Preparation of 3-(2-oxotetrahydrofuran-3-ylthio) propyl trifluoromethanesulfonate: 3-(3-Hydroxypropylthio) dihydrofuran-2(3H)-one (1.14 mL, 1.14 mmol) was dissolved in methylene chloride (1 mL), treated with 2,6-dimethylpyridine (0.290 ml, 2.50 mmol) and cooled to −10° C. under a $N_2$ atmosphere. Trifluoromethanesulfonic anhydride (0.401 mL, 2.38 mmol) dissolved in methylene chloride (1 mL) was added dropwise to the alcohol. After stirring for 90 minutes, the reaction mixture was quenched with 20% ethyl acetate/hexanes and the whole mixture was passed through a short silica gel column, eluting with ethyl acetate/hexanes (1:4). Concentration of the desired fractions in vacuo gave 3-(2-oxotetrahydrofuran-3-ylthio)propyl trifluoromethanesulfonate as a liquid (285 mg, 81%).

Step B: Preparation of 3-(2-oxotetrahydrofuran-3-ylthio) propyl analog of FK506: 3-(2-Oxotetrahydrofuran-3-ylthio) propyl trifluoromethanesulfonate (0.150 g, 0.488 mmol) was dissolved in methylene chloride (1 mL) and treated with 2,6-dimethylpyridine (0.0283 mL, 0.244 mmol). The solution was cooled to −20° C. and C32-thio-FK506 (0.100 g, 0.122 mmol) was added as a solution in methylene chloride (1 mL). The reaction was allowed to warm to ambient temperature with the cold bath and after stirring overnight, the reaction was poured into 10% $KHSO_4$ and diluted with additional methylene chloride. After separation, the organic layer was washed once with 10% $KHSO_4$, once with water, twice with 6% $NaHCO_3$, dried over $Na_2SO_4$ and concentrated in vacuo. The residue was chromatographed on silica gel eluting with 5% acetone/hexanes. The desired material was collected and concentrated to a white foam (0.040 g, 34%). MS (ESI+) m/z 1003 (M+Na) detected.

Example 27

IL-2 Inhibition Assay

The ability of the compounds of the present invention to inhibit IL-2 production may be determined by the following procedure. The human T lymphocyte cell line Jurkat are plated at a density of 200,000 cell per well in 96 well polypropylene plates. Fourfold serial dilutions of the test compounds were added to cover the desired concentration range which was adjusted depending on the potency of the compound (typically 0.001-2500 nM) and incubated for 1 hour at 37° C. Cells were then stimulated by the addition of the lectin phytohemagluttinin (10 μg/mL) and phorbol ester (100 ng/ml) and incubated for an additional 20 hours at 37° C. At the end of this incubation period supernatants are harvested by centrifuging plates for 10 minutes at 1500 rpm and are stored at −20° C. The IL-2 inhibition assay described above is performed in serum free growth media (RPMI containing L-glutamine, and 20 mM HEPES). IL-2 levels present supernatant from the above assay are determined using a commercial IL-2 ELISA (for example the Quantikine-human IL-2 immunoassay kit from R&D Systems) according to the manufacturers instructions. $IC_{50}$ values for inhibition of IL-2 production are determined for each compound tested from the inflexion point of a standard 4-parameter logistical curve fitted to the values obtained. All compounds disclosed herein had $IC_{50}$ values less than 1 micromolar.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof

What is claimed is:

1. A compound including resolved enantiomers, diastereomers; and pharmaceutically acceptable salts thereof, said compound having the Formula I:

wherein:
- X is alkyl, alkenyl, or alkynyl, wherein said alkyl, alkenyl and alkynyl are optionally substituted with one or more groups independently selected from F, Cl, Br, I, aryl, $COOR^1$, and a fully unsaturated or partially unsaturated five or six-membered heterocyclic ring having one to four heteroatoms independently selected from N, O and S, wherein said heterocyclic ring is optionally substituted with oxo;
- A is O;
- or A represents a carbon atom and an oxygen atom each bonded to carbon 32 of Formula I and which together complete a saturated or partially unsaturated five, six or seven membered spirocyclic lactone ring;
- Y is H or $R^3$—SC(=O),
- or Y is wherein said Y groups are optionally substituted with one or more groups independently selected from alkyl, alkenyl, alkynyl, $OR^4$, $SR^4$, and $NR^4R^5$; and
- L is alkylene, $Z_m$-E-Z, $NR^2C(=O)Z$, $C(=O)NR^2Z$, D-Ar—$NR^2C(=O)$, OArC(=O)CH$_2$, S-Z-NHC(=O) or wherein the asterisk indicates the point of attachment to Y; or Y is $R^3$—SC(=O) or Y is wherein said Y groups are optionally substituted with one or more groups independently selected from alkyl, alkenyl, alkynyl, $OR^4$, $SR^4$, and $NR^4R^5$ and
- L is absent, alkylene, $Z_m$-E-Z, $NR^2C(=O)Z$, $C(=O)NR^2Z$, D-Ar—$NR^2C(=O)$, OArC(=O)CH$_2$, S-Z-NHC(=O) or

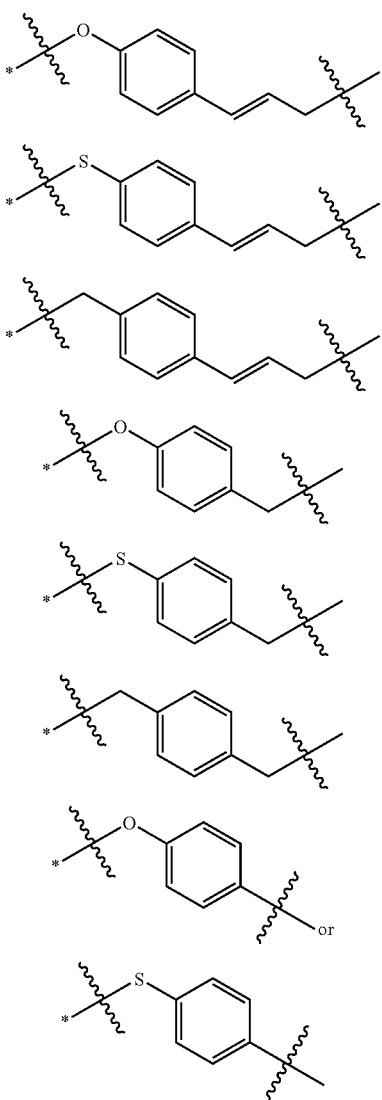

wherein the asterisk indicates the point of attachment to Y;

Z is $C_1$-$C_4$ alkylene optionally substituted with one or more groups selected from alkyl, F, Cl, Br or I;

Ar is arylene optionally substituted with one or more groups independently selected from F, Cl, Br and I;

D is $CH_2$, O, S, SO, or $SO_2$;

E is O, S, $NR^2$, or OC(=O);

m is 0 or 1;

j is 1, 2, 3, 4, or 5;

$R^1$ is H, alkyl, alkenyl, alkynyl, or aryl, wherein said aryl is optionally substituted with one or more groups independently selected from F, Cl, Br and I;

$R^2$ is H or alkyl;

$R^3$ is alkyl, alkenyl, or alkynyl, wherein said alkyl, alkenyl, and alkynyl are optionally substituted with one or more groups independently selected from F, Cl, Br, and I; and $R^4$ and $R^5$ are independently H, alkyl or aryl.

2. The compound of claim 1, wherein A is O.

3. The compound of claim 2, wherein Y is

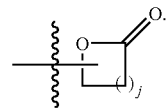

4. The compound of claim 2, wherein Y is selected from the structures:

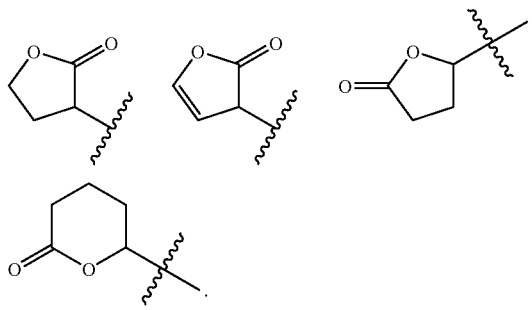

5. The compound of claim 4, wherein L is absent.

6. The compound of claim 4, wherein L is optionally substituted alkylene.

7. The compound of claim 6, wherein L is optionally substituted methylene, ethylene, or propylene.

8. The compound of claim 4, wherein L is $Z_m$-E-Z.

9. The compound of claim 8, wherein L is

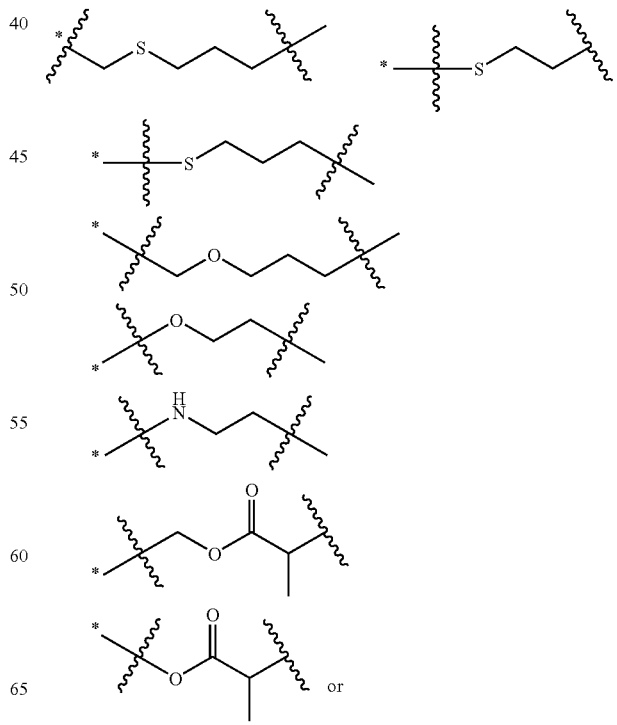

-continued

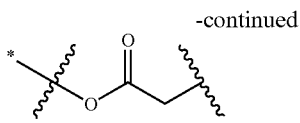

wherein the asterisk indicates the point of attachment to Y.

10. The compound of claim 4, wherein L is NR²C(=O)Z.
11. The compound of claim 10, wherein L is

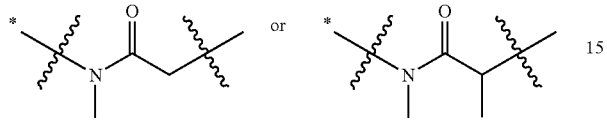

wherein the asterisk indicates the point of attachment to Y.

12. The compound of claim 1, wherein L is

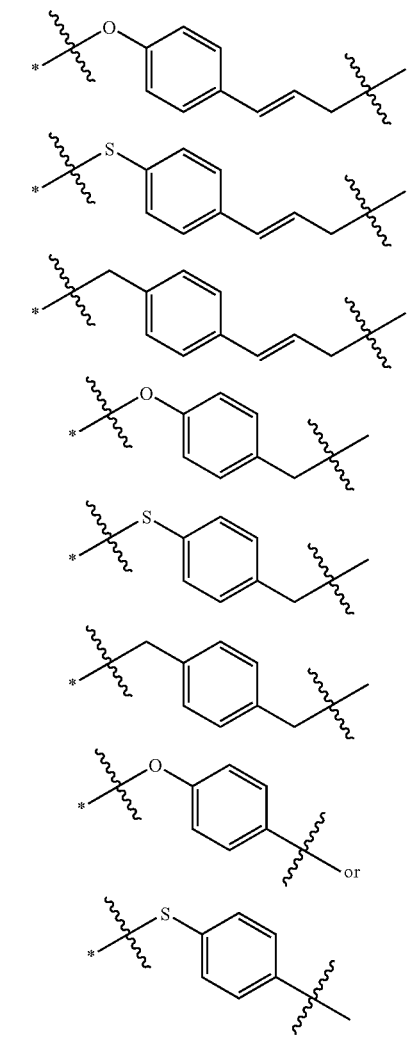

where in the asterisk indicates the point of attachment to Y.

13. The compound of claim 4, wherein L is D-Ar-NR²C(=O).

14. The compound of claim 13, wherein L is

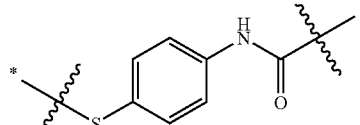

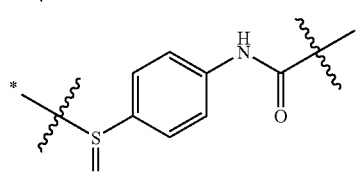

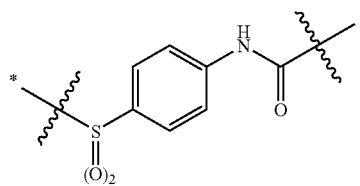

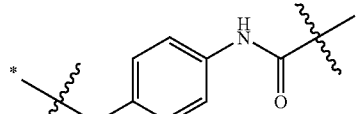

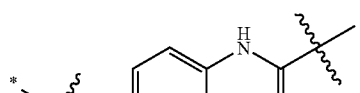

or

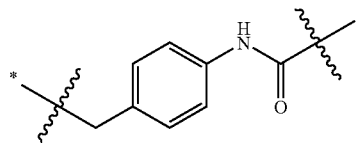

wherein the asterisk indicates the point of attachment to Y.

15. The compound of claim 4, wherein L is OArC(=O)CH₂.

16. The compound of claim 15, wherein L is

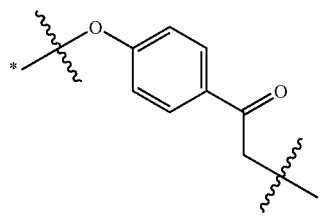

wherein the asterisk indicates the point of attachment to Y.

17. The compound of claim 4, wherein L is S-Z-NHC(=O).

18. The compound of claim 17, wherein L is

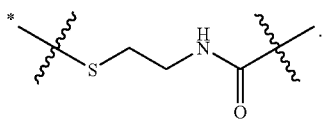

19. The compound of claim 2, wherein Y is selected from the structures:

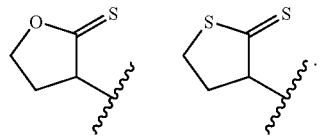

20. The compound of claim 2, wherein X is an optionally substituted alkyl or allyl.

21. The compound of claim 20, wherein X is methyl, ethyl.

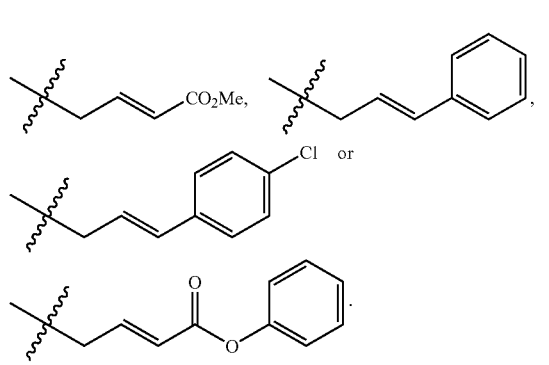

22. The compound of claim 1, selected from the structures

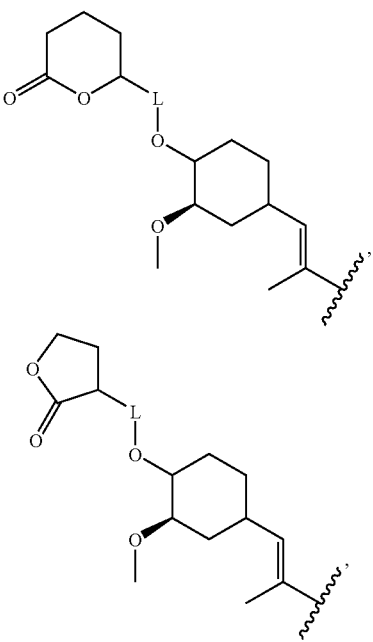

-continued

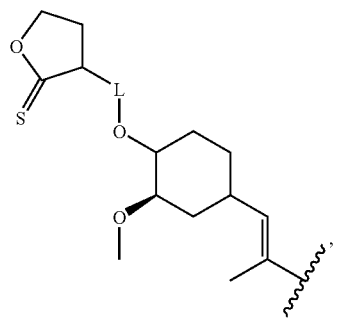

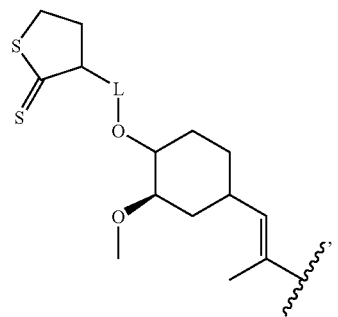

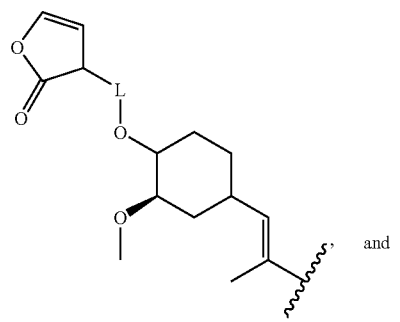

and

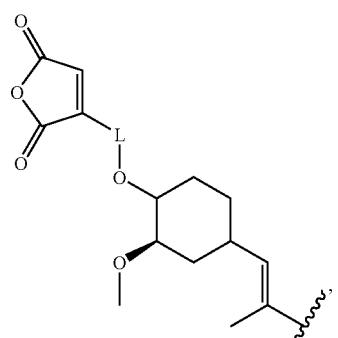

wherein the wavy line indicates the point of attachment to the macrocyclic core.

23. The compound of claim 1, selected from the structures:
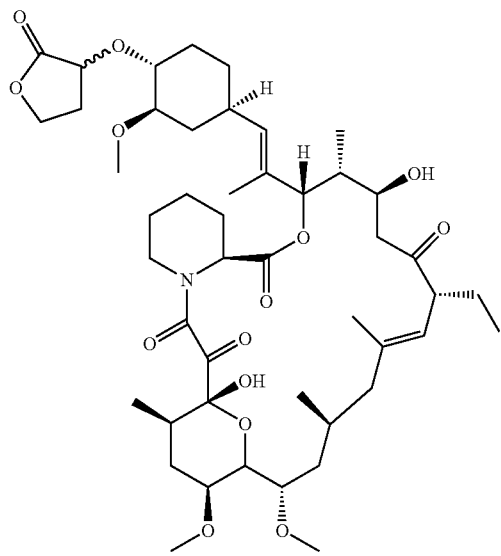
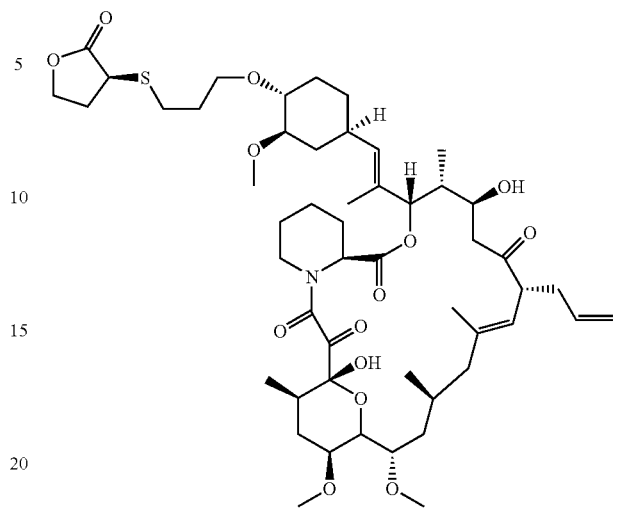
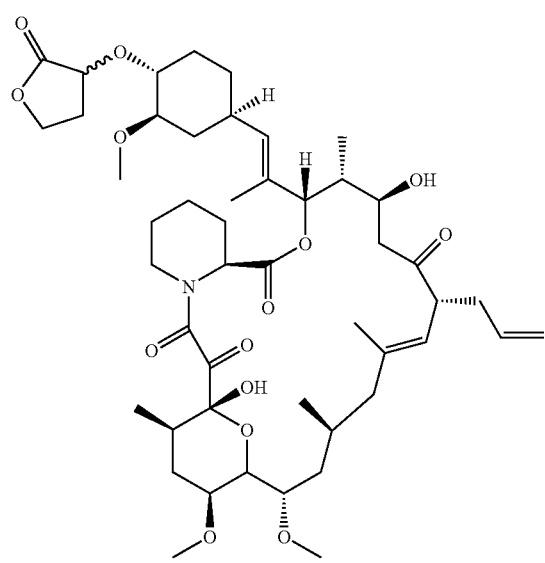
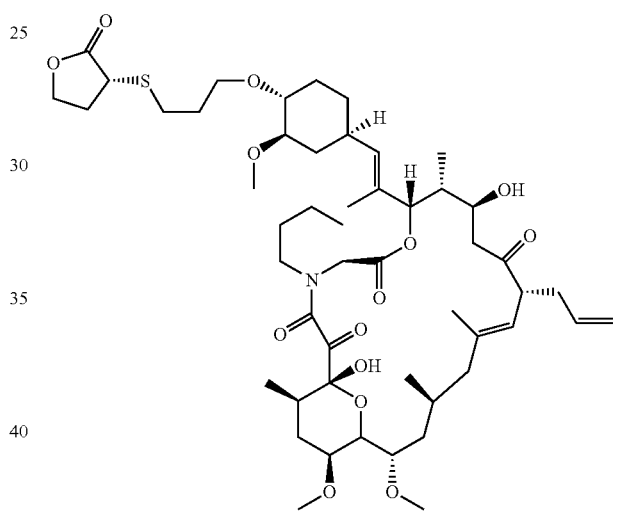
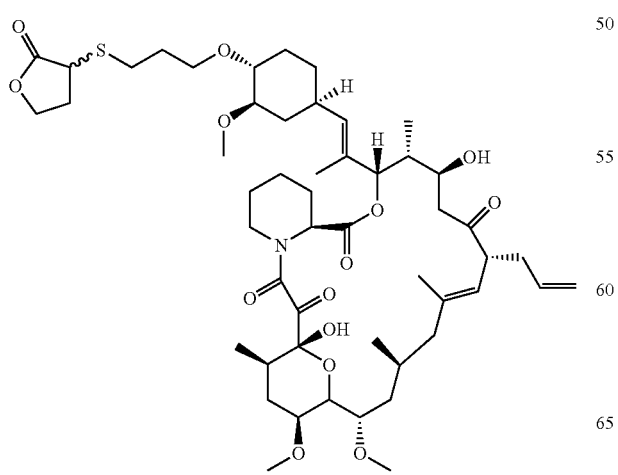
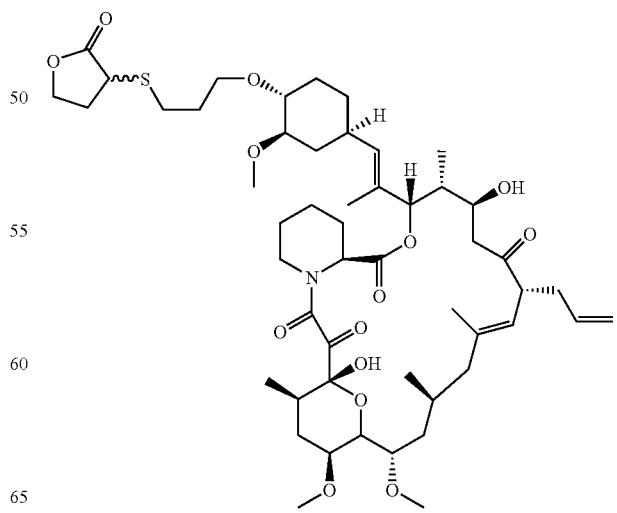

67
-continued
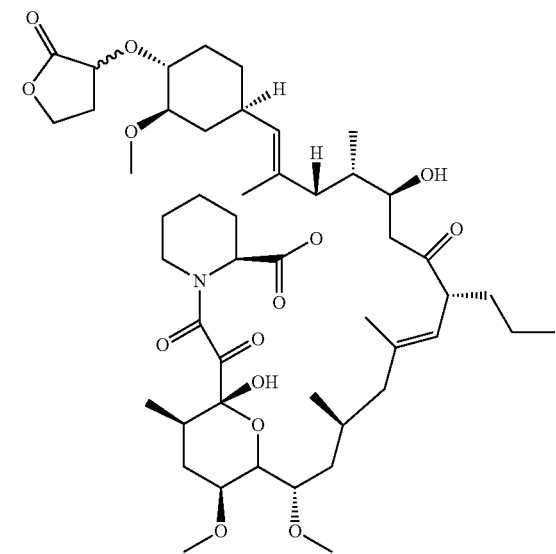
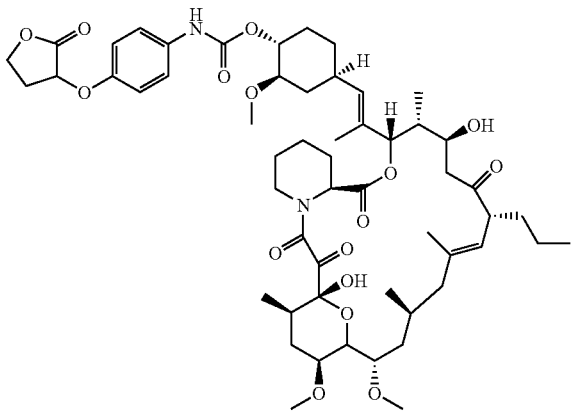
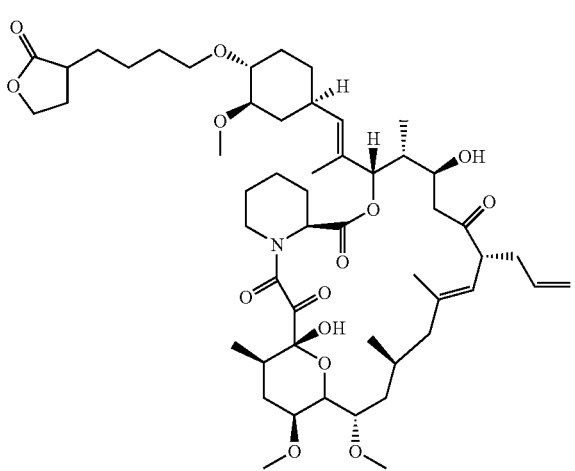
68
-continued
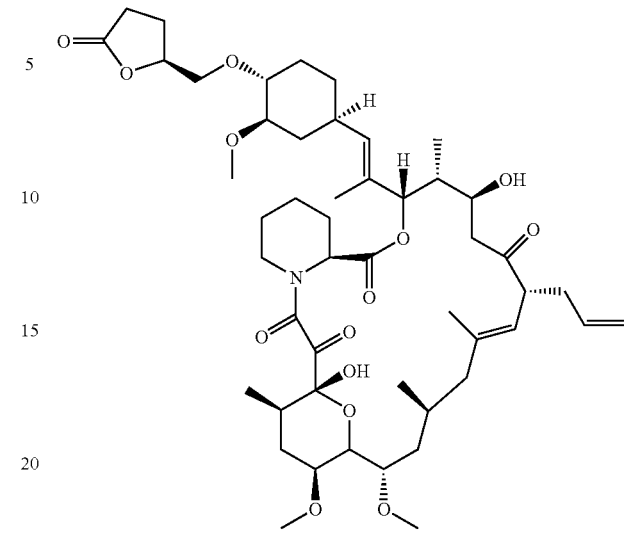
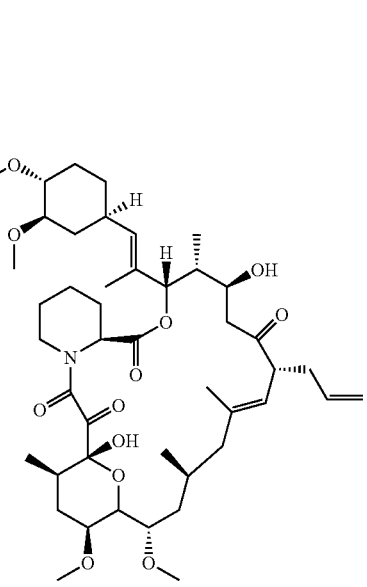

-continued

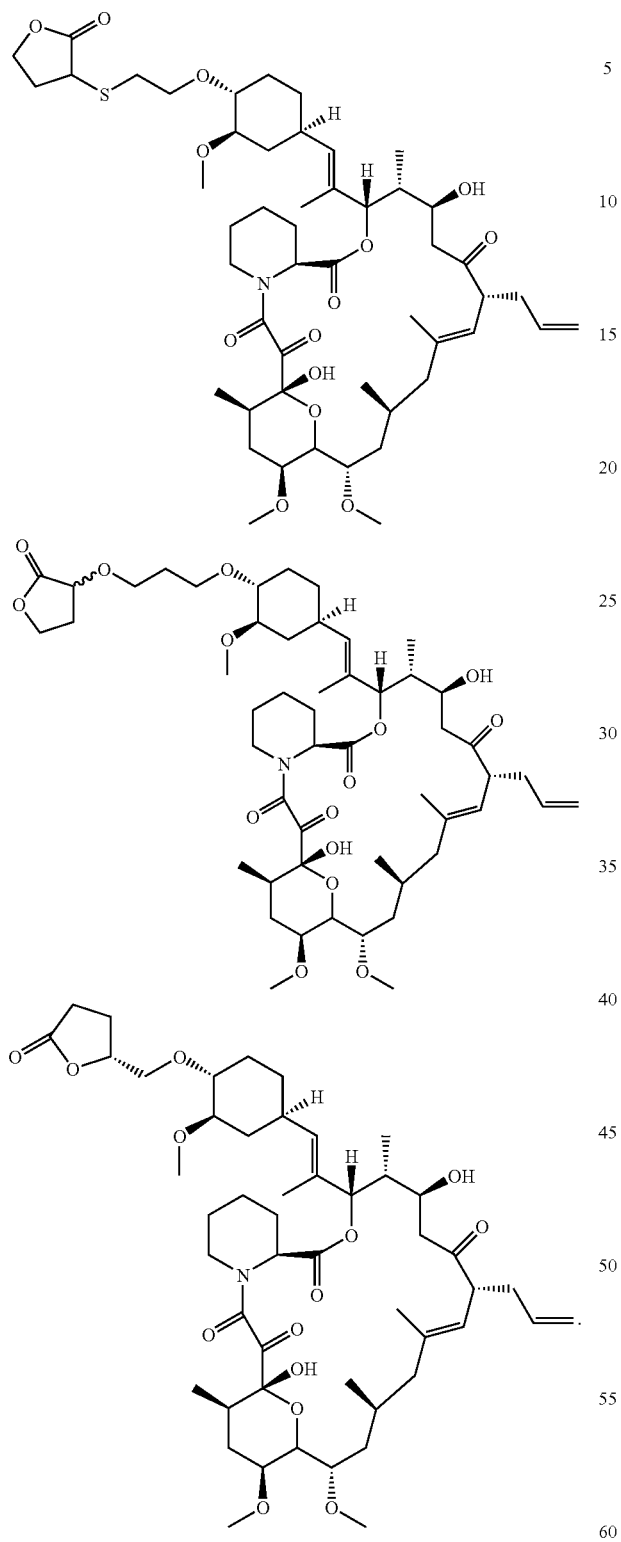

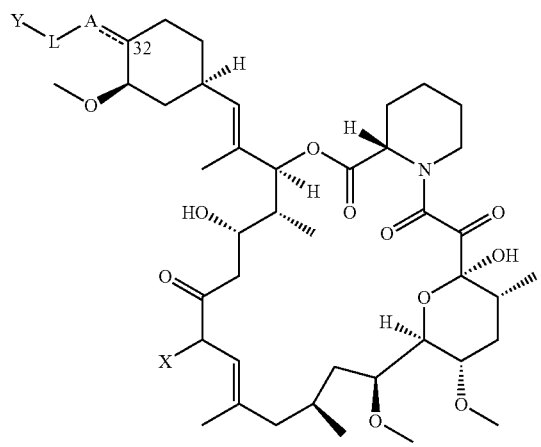

wherein:
the dashed line is an optional double bond;
X is alkynyl, wherein said alkynyl is optionally substituted with one or more groups independently selected from F, Cl, Br, I, aryl, COOR$^1$, and a fully unsaturated or partially unsaturated five or six-membered heterocyclic ring having one to four heteroatoms independently selected from N, O and S, wherein said heterocyclic ring is optionally substituted with oxo;
A is O,
or A represents a carbon atom and an oxygen atom each bonded to carbon 32 of Formula I and which together complete a saturated or partially unsaturated five, six or seven membered spirocyclic lactone ring;
Y is absent, H, R$^3$—SC(=O) or R$^3$—OC(=O),
or Y is

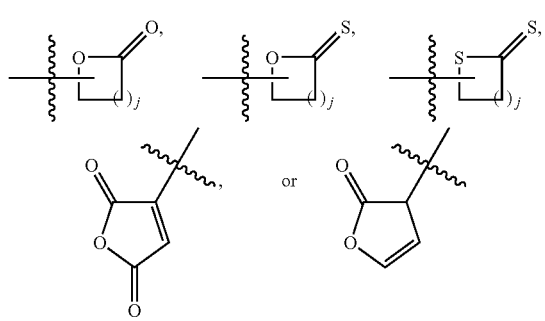

wherein said Y groups are optionally substituted with one or more groups independently selected from alkyl, alkenyl, alkynyl, OR$^4$, SR$^4$, and NR$^4$R$^5$;
L is absent, alkylene, $Z_m$-E-Z, NR$^2$C(=O)Z, C(=O)NR$^2$Z, D-Ar—NR$^2$C(=O), OArC(=O)CH$_2$, S-Z-NHC(=O) or

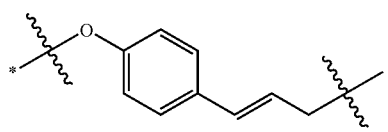

24. A composition comprising a compound of claim 1 and a pharmaceutically acceptable carrier.

25. A compound including resolved enantiomers, diastereomers and pharmaceutically acceptable salts thereof, said compound having the Formula I:

-continued

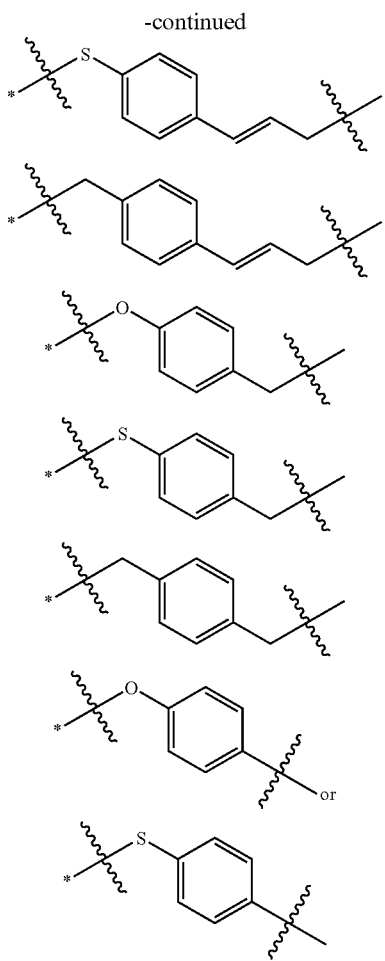

wherein the asterisk indicates the point of attachment to Y;

Z is $C_1$-$C_4$ alkylene optionally substituted with one or more groups selected from alkyl, F, Cl, Br or I;

Ar is arylene optionally substituted with one or more groups independently selected from F, Cl, Br and I;

D is $CH_2$, O, S, SO, or $SO_2$;

E is O, S, $NR^2$, or OC(=O);

m is 0 or 1;

j is 1, 2, 3, 4, or 5;

$R^1$ is H, alkyl, alkenyl, alkynyl, or aryl, wherein said aryl is optionally substituted with one or more groups independently selected from F, Cl, Br and I;

$R^2$ is H or alkyl;

$R^3$ is alkyl, alkenyl, or alkynyl, wherein said alkyl, alkenyl, and alkynyl are optionally substituted with one or more groups independently selected from F, Cl, Br, and I; and $R^4$ and $R^5$ are independently H, alkyl or aryl.

26. A compound having the structure:

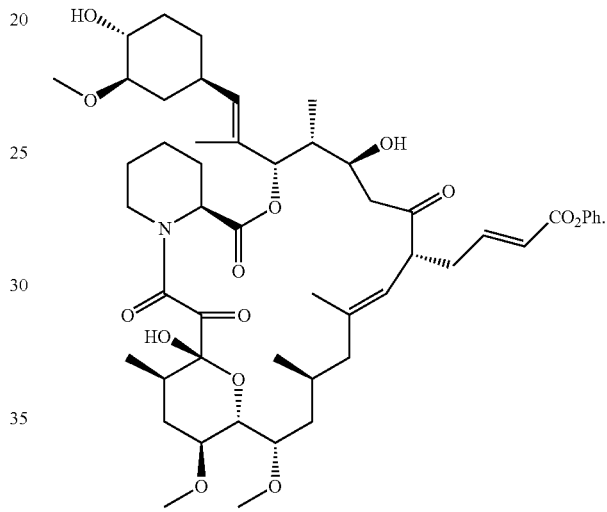

* * * * *